US006248519B1

(12) United States Patent
Engel et al.

(10) Patent No.: US 6,248,519 B1
(45) Date of Patent: *Jun. 19, 2001

(54) DETECTION OF FERMENTATION-RELATED MICROORGANISMS

(75) Inventors: Stacia R. Engel; Richard A. Descenzo; Richard A. Morenzoni; Nancy A. Irelan, all of Modesto, CA (US)

(73) Assignee: E & J Gallo Winery, Modesto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

(21) Appl. No.: 09/037,990

(22) Filed: Mar. 11, 1998

(51) Int. Cl.[7] .............................. C12Q 1/68; C07H 21/04

(52) U.S. Cl. ........................... 435/6; 435/91.2; 536/23.1; 536/24.3; 536/24.32

(58) Field of Search ..................... 435/6, 91.2; 536/24.3, 536/23.1, 24.32

(56) References Cited

U.S. PATENT DOCUMENTS

| | | | |
|---|---|---|---|
| 4,230,625 | 10/1980 | Despreaux et al. | 260/397.1 |
| 4,301,246 | 11/1981 | Despreaux et al. | 435/58 |
| 5,149,624 | 9/1992 | Gabriel | 435/6 |
| 5,389,513 | 2/1995 | Baquero et al. | 435/6 |
| 5,389,515 | 2/1995 | Chmelo et al. | 435/6 |
| 5,403,710 | 4/1995 | Weisburg et al. | 435/6 |
| 5,426,027 | 6/1995 | Lott et al. | 435/6 |
| 5,434,048 | 7/1995 | Simon et al. | 435/6 |
| 5,545,525 | 8/1996 | Montplaisir et al. | 435/6 |
| 5,580,971 | 12/1996 | Mitsuhashi | 536/24.32 |
| 5,585,238 * | 12/1996 | Lignon et al. | 435/6 |
| 5,622,827 | 4/1997 | McAllister et al. | 435/6 |
| 5,627,275 | 5/1997 | Roll | 536/23.7 |
| 5,631,132 | 5/1997 | Lott et al. | 435/6 |
| 5,635,353 | 6/1997 | Lott et al. | 435/6 |
| 5,792,611 | 8/1998 | Hamelin | 435/6 |

FOREIGN PATENT DOCUMENTS 2 781 812   7/1998   (FR) .

OTHER PUBLICATIONS

White et al., "Amplification and Direct Sequencing of Fungal Ribosomal RNA Genes for Phylogenetics", PCR Protocols: A Guide to Methods and Applicatons, pp. 315–322, (1989).

Holst–Jensen et al., "Molecular phylogeny and evolution of Monilinia . . . ", Am. Journal of Botany, 84 (5), 686–701, 1997.*

Boysen et al., "Reclassification of the Penicillium roqueforti group . . . ", Microbiology, 142, 541–549, 1996.*

Oda et al., "A phylogenetic Analysis of Saccharomyces Species . . . ", Yeast, 13, 1243–1250, 1997.*

Baleiras Couto et al., "Evaluation of Molecular Typing Techniques to Assign Genetic Diversity . . . ", Appl. Environmental Microbiology, 61(1), 41–46, Jan. 1996.*

Holst–Jensen, Genbank Accession No. Z73765, May 1996.*

Peterson, Genbank Accession No. AF033472, Nov. 1997.*

Peterson, Genbank Accession No. AF034453, Nov. 1997.*

Williams, Genbank Accession No. L47113, 1995.*

Messner, Genbank Accession No. U09327, May 1994.*

Boysen, Genbank Accession No. X82361, Oct. 1994.* de Barros Lopes et al, "PCR Differentiation of Commercial Yeast Strains Using Intron Splice Site Primers", Appl. and Environ. Microbiol., 62:4514–4520, 1996.

Fell, "Rapid Identification of Yeast Species Using Three Primers in a Polymerase Chain Reaction", Molecular Marine Biology and Biotechnology, 2(3):174–180, 1993.

Fell, "rDNA Targeted Oligonucleotide Primers for the Identification of Pathogenic Yeasts in a Polymerase Chain Reaction", J. of Industrial Microbiol., 14:475–477, 1995.

Ibeas et al, "Detection of Dekkera–Brettanomyces Strains in a Sherry by a Nested PCR Method", Appl. and Environ. Microbiol, 62:998–1003, 1996.

Lavalée et al, "PCR and DNA Fingerprinting Used as Quality Control in the Production of Wine Yeast Strains", Am. J. Enol. Vitic., 45(1), 86–91, 1994.

Lieckfeldt et al, "Rapid Identification and Differentiation of Yeasts by DNA and PCR Fingerprinting", J. Basic Microbiol., 33(6):413–426, 1993.

Ness et al, "Identification of Yeast Strains Using the Polymerase Chain Reaction", J. Sci. Food Agric., 62:89–94, 1993.

Casey et al, "Evaluation of Recent Techniques Used to Identify Individual Strains of Saccharomyces Yeasts", J. of the ASBC, 48(3): 100–105.

Degré et al, "Wine Yeasts Strain Identification", Am. J. Enol. Vitic., 40(4), 309–315, 1989.

Guillamón et al, "Characterization of Wine Yeast Strains of the Saccharomyces Genus on the Basis of Molecular Markers: Relationships Between Genetic Distance and Geographic or Ecological Origin", System. Appl. Microbiol., 19:122–132, 1996.

(List continued on next page.)

Primary Examiner—Lisa B. Arthur
Assistant Examiner—Jeanine Goldberg
(74) Attorney, Agent, or Firm—Marshall, O'Toole, Gerstein, Murray & Borun

(57) ABSTRACT

DNA sequences are provided which are useful in identifying different fermentation-related microorganisms, such as those involved in fermentations. These DNA sequences can be used to provide oligonucleotide primers in PCR based analysis for the identification of fermentation-related microorganisms. The DNA sequences of the present invention include the internal transcribed spacer (ITS) of the ribosomal RNA gene regions of particular fermentation-related microorganisms, as well as oligonucleotide primers which are derived from these regions which are capable of identifying the particular microorganism.

45 Claims, No Drawings

OTHER PUBLICATIONS

Hoeben et al, "An Approach to Yeast Classification by Mapping Mitochondrial DNA from Dekkera/Brettanomyces and *Eeniella genera*", Curr. Genet, 10:371–379, 1986.

Možina et al, "Identification of *Saccharomyces sensu stricto* and Torulaspora Yeasts by PCR Ribotyping", Letters in Applied Microbiol., 24: 311–315, 1997.

Paffetti et al, "DNA Fingerprinting by Random Amplified Polymorphic DNA and Restriction Fragment Length Polymorphism is Useful for Yeast Typing", Res. Microbiol., 146:587–594, 1995.

Panchal et al, "A Rapid, Simple and Reliable Method of Differentiating Brewing Yeast Strains Based on DNA Restriction Patterns", J. Inst. Brew., 93:325–327, 1987.

Querol et al, "A Comparative Study of Different Methods of Yeast Strain Characteriation", System Appl. Microbiol., 15:439–446, 1992.

Vezinhet et al, "Chromosomal DNA Patterns and Mitochondrial DNA Polymorphism as Tools for Identification of Enological Strains of *Saccharomyces cervisiae*", Appl. Microbiol. Biotechnol., 32:568–571, 1990.

Vezinhet et al, "Ecological Survey of Wine Yeast Strains by Molecular Methods of Identification", Am. J. Enol. Vitic., 43(1):83–86, 1992.

Vaughan–Martini et al, Differential Killer Sensitivity as a Tool for Fingerprinting Wine–Yeast Strains of *Saccharomyces cervisiae*. J. of Industrial Microbiol., 17:124–127, 1996.

H.H. Albert et al, "PCR Amplification from a Homolog of the bE Mating–Type Gene as a Sensitive Assay for the Presence of . . . DNA", Plant Dis., 80(10):1189–1192, 1996.

E. Wheeler Alm, "The Oligonucleotide Probe Disease", Appl. and Environ. Microbiol., 62(10):3557–3559, 1996.

J.M. Rodriguez, "PCR Detection of the Lactocin S Structural Gene in Bacteriocin–Producing Lactobacilli from Meat", Appl. and Environ. Microbiol., 61(7):2802–2805.

R.Y.C. Kong et al, "Co–detection of Three Species of Water–Borne Bacteria by Multiplex PCR", Marine Pollution Bulletin, Elsevier Science Ltd., 1995.

R.P. Doss et al, "A Polymerase Chain Reaction–Based Procedure for Detection of Acremonium coenophialum in Tall Fescue", Phytopathology, 85(8):913–917, 1995.

F. Niepold et al, "Application of the PCR technique to detect Phytophthora infestans in potato tubers and leaves", Microbiol. Res., 150(4):379–385, 1995.

P. Audy et al, "A Rapid and Sensitive PCR–Based Assay for Concurrent Detection of Bacteria Causing Common and Halo Blights in Bean Seed", Phytopathology, 86(4):361–366, 1996.

P.M. Border et al, "Detection of Listeria species and Listeria monocytogenes using polymerase chain reaction", Letters in Appl. Microbiol., 11:158–162, 1990.

J.L. Ibeas et al, "Detection of Dekkera–Brettanomyces Strains in Sherry by a Nested PCR Method", Appl. and Environ. Microbiol., 62(3):998–1003, 1996.

P. Muncan et al, Early Identification of Candiduria by Polymerase Chain Reaction in High Risk Patients, J. of Urology, 156:154–156, 1996.

G. Schönian et al, "Identification of clinical strains of *Candida albicans* by DNA fingerprinting with the polymerase chain reaction", Mycoses, 36:171–179, 1993.

H. Tsen et al, "Possible Use of a Polymerase Chain Reaction Method for Specific Detection of Salmonella in Beef", J. of Fermentation and Bioengineering, 77(2):137–143, 1994.

L.M. Tuchili et al, "Detection of Salmonella DNA in Chicken Embryos and Environmental Samples by Polymerase Chain Reaction", J. Vet. Med. Sci., 58(9):881–884, 1996.

M. Mazzola et al, "Virulence of *Rhizoctonia oryzae* and *R. solani* AG–8 on Wheat and Detection of *R. oryzae* in Plant Tissue by PCR", Phytopathology, 86(4):354–360, 1996.

M.V. Carter et al, "An annotated host list bibliography of *Eutypa armeniacae*", Review of Plant Pathology, 62(7), 1983.

S.K. Sood et al, "PCR–based detection of Listeria monocytogenes in dairy foods", Current Science, 71(6):449–456, 1996.

Gardes et al, "ITS–RFLP Matching for Identification of Fungi", Methodsin Molecular Biol., 50:177–186, 1996.

Y. Kumeda et al, "Single–Strand Conformation Polymorphism Analysis of PCR–Amplified Ribosomal DNA . . . Flavi", Appl. and Envir. Microbiol., 62(8):2947–2952.

M. Gardes et al, "ITS primers with enhanced specificity for basidiomycetes–application to the identification of mycorrhizae and rusts", Molecular Ecology, 2:113–118, 1993.

R.C. Hamelin et al, "Identification of Root Rot Fungi in Nursery Seedlings by Nested Multiplex PCR", Appl. and Environ.. Microbiol., 62(11):4026–4031, 1996.

D. O'Gorman et al, "Detection of *Leptosphaeria korrae* with the polymerase chain reaction and primers fromribosomal internal transcribed spacers", Can. J. Bot., 72:342–346, 1994.

N.L. Glass et al, "Development of Primer Sets Designed for Use with the PCR to Amplify Conserved Genes . . . Ascomycetes", Appl. and Environ. Microbiol., 61(4):1323–1330, 1995.

T.J. White et al, "Amplification and Direct Sequencing of Fungal Ribosomal RNA Genes for Phylogenetics", PCR Protocols: A Guide to Methods and Appl., 315–322, 1990.

D.J. Appel et al, "Relationships Among Pathogenic and Nonpathogenic Isolates of *Fusarium oxysporum* based on the Partial Sequence . . . DNA", MPMI, 9(2):125–138, 1996.

L. Simon, "Specific PCR Primers for the Identification of Endomycorrhizal Fungi", Methods in Molecular Biol., 50:187–192, 1996.

K.–N. Li et al, "PCR Primers that allow Intergeneric Differentiation of Ascomycetes and their Application to Verticillium spp.", Appl. and Environ. Microbiol., 60(12):4324–4331, 1994.

D.L. Davies et al, "Detection of Phytoplasmas Associated with Pear Decline in Pear Psyllids by Polymerase Chain Reaction", BCPC Symposium Proceedings, 65:67–72, 1996.

T.J. Walsh et al, "PCR and Single–Strand Conformational Polymorphism for Recognition of Medically Important Opportunistic Fungi", J. of Clinical Microbiol., 33(12):3216–3220, 1995.

T. Nakagawa et al, "Detection of Alcohol–Tolerant Hoichi Bacteria by PCR", Appl. and Environ. Microbiol., 60(2):637–640, 1994.

T. Graham et al, "Genus– and species–specific detection of Listeria monocytogenes using polymerase chain reaction assays . . . operon", Can. J. Microbiol., 42:1155–1162, 1996.

M. Maiwald et al, "Rapid presumptive identification of medically relevant yeasts to the species level . . . enzyme analysis", J. of Medical and Veterinary Mycology, 32:115–122, 1994.

C. Prariyachatigul et al, "Assessment of a PCR technique for the detection and identification of *Cryptococus neoformans*", J. of Medical and Veterinary Mycology, 34:251–259, (1996).

Q. Zhu et al, "Detection of *Salmonella typhi* by polymerase chain reaction", J. of Applied Bacteriology, 80:244–251, 1996.

C.D. Smart et al, "Phytoplasma–Specific PCR Primers Based on Sequences of the 16S–23S rRNA Spacer Region", Appl. and Environ. Microbiol., 62(8):2988–2993, 1996.

M.E. Omunyin, "Use of Unique RNA Sequence–Specific Oligonucleotide Primers for RT–PCR to Detect and Differentiate Soybean Mosaic Virus Strains", Plant Dis., 80(10):1170–1174.

* cited by examiner-

# DETECTION OF FERMENTATION-RELATED MICROORGANISMS

FIELD OF THE INVENTION

The present invention relates to assays to detect fermentation-related microorganisms.

DESCRIPTION OF THE RELATED ART

In traditional wine-making, the indigenous yeasts ferment the grape must. Most modern wine-makers, however, inoculate with a pure culture of a selected yeast strain to ensure a rapid, reliable and predictable fermentation. It is thought that indigenous yeasts are suppressed by the competitive effect of addition of a high-density monoculture, but some evidence suggests that indigenous yeast can still participate in the fermentation. A range of commercial yeasts with different wine-making characteristics is available, and a number of those yeast strains may be used in a single winery. Furthermore, unwanted microorganisms may be present which lead to spoilage. Therefore, there is a need for a rapid, simple and accurate method for identifying microorganisms in starter cultures and fermentations.

Past techniques for detecting and identifying fermentation-related microorganisms, especially yeast, include colony morphology, fermentation performance, sugar fermentation tests, tolerance to various stresses (e.g., ethanol tolerance in brewing), phenotypes with functional relevance (e.g., flocculation in brewing), nutritional requirements (e.g., oxygen), and resistance and sensitivity levels of cycloheximide. These methods, however, have numerous disadvantages, including lengthy analysis periods, inability to differentiate, e.g., different strains of yeast, and lack of reproducibility.

Recent developments in molecular biology and protein chemistry have provided new methods for identifying microorganisms, including DNA restriction fragment length polymorphisms, protein electrophoresis patterns and chromosome fingerprinting. Such techniques have been used for identifying fermentation-related microorganisms. See, for example, Casey et al, *Journal of the American Society of Brewing Chemists*, 48(3):100–106, 1990; Degre et al, *American Journal of Enology and Viticulture*, 40(4) 309–315, 1989; Guillamon et al, *Systematic and Applied Microbiology*, 19:122–132, 1992; Hoeben et al, *Current Genetics*, 10:371–379, 1986; Mozina et al, *Letters in Applied Microbiology*, 24(4):311–315, 1997; Paffetti et al, *Research Microbiology*, 146:587–594, 1995; Panchal et al, *Journal of the Institute of Brewing*, 93:325–327, 1987; Querol et al, *Systematic and Applied Microbiology*, 15:439–446, 1992; Vezinhet et al, *Applied Microbiology and Biotechnology*, 32:568–571, 1990; and Vezinhet et al, *American Journal of Enology and Viticulture*, 43(1):83–86, 1992.

Polymerase chain reaction (PCR)-based techniques have also been used to detect fermentation-related microorganisms. See, for example, DeBarros Lopes et al, *Applied and Environmental Microbiology*, 62(12):4514–4520, 1996; Fell, *Molecular Marine Biology and Biotechnology*, 2(3) 174–180, 1993; Fell, *Journal of Industrial Microbiology*, 14(6):475–477, 1995; Ibeas et al, *Applied and Environmental Microbiology*, 62(3):998–1003, 1996; Lavallee et al, *American Journal of Enology and Viticulture*, 45(1):86–91, 1994; Lieckfeldt et al, *Journal of Basic Microbiology*, 33(6) 413–425, 1993; and Ness et al, *J. Sci. Food Agric.*, 62:89–94, 1993.

Ribosomal genes are suitable for use as molecular probe targets because of their high copy number. Non-transcribed and transcribed spacer sequences associated with ribosomal genes are usually poorly conserved and, thus, are advantageously used as target sequences for the detection of recent evolutionary divergence. Fungal rRNA genes are organized in units. Each unit encodes mature subunits of 18S, 5.8S, and 28S rRNA. The internal transcribed spacer (ITS) region lies between the 18S and 28S rRNA genes and contains two variable non-coding spacers (referred to as ITS1 and ITS2) and the 5.8S rRNA gene (White et al., 1990; In: *PCR Protocols*; Eds.: Innes et al.; pages 315–322). In addition, the transcriptional units are separated by non-transcribed spacer sequences (NTSs). The ITS and NTS sequences are particularly suitable for the detection of different fungal pathogens.

Kumeda et al (*Applied and Environmental Microbiology*, 62(8):2947–2952, 1996) describes use of PCR to amplify ribosomal DNA internal transcribed spacers in order to differentiate species of Aspergillus Section Flavi. The ITS1-5.8S-ITS2 region was amplified using universal primers, and the PCR product analyzed by the principle of single-strand conformation polymorphism. In addition, Gardes et al (in: *Methods in Molecular Biology, Vol. 50: Species Diagnostics Protocols: PCR and Other Nucleic Acid Methods*, Ed. J. P. Clapp, Humana Press, Totowa, N.J., (1996) pp. 177–186) describes restriction fragment length polymorphism (RFLP) analysis of fungal ITS regions amplified by PCR.

The PCR amplification of fungal ITS has also been described using other than universal primers. These methods allow for more specificity in identifying classes of fungi, or particular species of fungi. Thus, Gardes and Bruns (*Molecular Ecology*, 2:113–118, 1993) identified ITS primers which allow differentiation of DNA from basidiomycetes against ascomycete DNA. Identification of specific species has been observed using PCR primers directed to unique sequences in the ITS1 and/or ITS2 regions of fungal pathogens. See, for example, Hamelin et al, *Applied and Environmental Microbiology*, 62(11):4026–4031, 1996; Mazzola et al, *Phytopathology*, 86(4):354–360, 1996; O'Gorman et al, *Canadian Journal of Botany*, 72:342–346, 1994; and U.S. Pat. No. 5,585,238 to Ligon et al.

The present invention addresses the problem of detecting and identifying fermentation-related microorganisms by PCR-based techniques.

SUMMARY OF THE INVENTION

The present invention is directed to the identification of different fermentation-related microorganisms, particularly those involved in the production of wine. The present invention provides DNA sequences which exhibit variability between different fermentation-related microorganisms. In particular, the present invention identifies regions of DNA sequence located in the internal transcribed spacer (ITS) of the ribosomal RNA gene regions of various fermentation-related microorganisms. Primers derived from the ITS can be used in polymerase chain reaction (PCR) based diagnostic assays to determine the presence or absence of specific fermentation-related microorganisms, including those involved in the production of wine. The primers can also be used as molecular probes to detect the presence of target DNA.

Thus, in one aspect, the present invention provides an isolated double stranded nucleic acid of the full length ITS1 or ITS2 region of a fermentation-related microorganism. More particularly, the DNA sequence is selected from among Sequence ID NOS: 13 to 36.

In another aspect, the present invention provides an oligonucleotide primer for identification of a fermentation-related microorganism, wherein the primer is a divergent portion of the ITS1 or ITS2 region of a fermentation-related microorganism. More particularly, the oligonucleotide primer is selected from among Sequence ID NOS: 65 to 98. Furthermore, the oligonucleotide primers may be selected from among sequences which contain at least 10 contiguous nucleotide bases from one of SEQ ID NOS: 65 to 98, primers which contain at least 10 contiguous nucleotide bases from one of SEQ ID NOS: 65 to 98 contiguous with 1 to 15 nucleotide bases in the 5' and/or 3' direction of corresponding SEQ ID NOS: 37 to 64, and primers of 10 nucleotide bases or longer which contain at least 5 contiguous nucleotide bases from one of SEQ ID NOS: 65 to 98 contiguous with from 1 to 15 nucleotide bases in the 5' and/or 3' direction of corresponding SEQ ID NOS: 37 to 64. A pair of the foregoing oligonucleotide primers for use in the amplification-based detection of an ITS of a fermentation-related microorganism is also provided.

In yet another aspect, a method is provided for detection of a fermentation-related microorganism which comprises: (a) obtaining DNA from a fungal culture or colony isolated from a fermentation, or from an organism present in a fermentation beverage; (b) amplifying a part of the ITS of the fermentation-related microorganism using the DNA as a template in a polymerase chain reaction with the aforementioned oligonucleotide primers; and (c) visualizing the amplified part of the ITS sequence to determine whether the fermentation-related microorganism is present.

In still another aspect, kits are provided which are useful in detecting fermentation-related microorganisms.

BRIEF DESCRIPTION OF THE SEQUENCES IN THE SEQUENCE LISTING

SEQ ID NO: 1 DNA sequence for the internal transcribed spacer of *Saccharomyces cerevisiae* and *Saccharomyces bayanus*.

SEQ ID NO: 2 DNA sequence for the internal transcribed spacer of *Saccharomycodes ludwigii*.

SEQ ID NO: 3 DNA sequence for the internal transcribed spacer of *Dekkera bruxellensis*.

SEQ ID NO: 4 DNA sequence for the internal transcribed spacer of *Dekkera intermedia*.

SEQ ID NO: 5 DNA sequence for the internal transcribed spacer of *Botrytis cinerea*.

SEQ ID NO: 6 DNA sequence for the internal transcribed spacer of *Penicillium crustosum*.

SEQ ID NO: 7 DNA sequence for the internal transcribed spacer of *Penicillium expansum*.

SEQ ID NO: 8 DNA sequence for the internal transcribed spacer of *Hanseniaspora guilliermondii*.

SEQ ID NO: 9 DNA sequence for the internal transcribed spacer of *Debaryomyces carsonii*.

SEQ ID NO: 10 DNA sequence for the internal transcribed spacer of *Pichia anomala*.

SEQ ID NO: 11 DNA sequence for the internal transcribed spacer of *Pichia kluyveri*.

SEQ ID NO: 12 DNA sequence for the internal transcribed spacer of *Candida krusei*.

SEQ ID NO: 13 DNA sequence for the ITS1 of *Saccharomyces cerevisiae* and *Saccharomyces bayanus*.

SEQ ID NO: 14 DNA sequence for the ITS2 of *Saccharomyces cerevisiae* and *Saccharomyces bayanus*.

SEQ ID NO: 15 DNA sequence for the ITS1 of *Saccharomycodes ludwigii*.

SEQ ID NO: 16 DNA sequence for the ITS2 of *Saccharomycodes ludwigii*.

SEQ ID NO: 17 DNA sequence for the ITS1 of *Dekkera bruxellensis*.

SEQ ID NO: 18 DNA sequence for the ITS2 of *Dekkera bruxellensis*.

SEQ ID NO: 19 DNA sequence for the ITS1 of *Dekkera intermedia*.

SEQ ID NO: 20 DNA sequence for the ITS2 of *Dekkera intermedia*.

SEQ ID NO: 21 DNA sequence for the ITS1 of *Botrytis cinerea*.

SEQ ID NO: 22 DNA sequence for the ITS2 of *Botrytis cinerea*.

SEQ ID NO: 23 DNA sequence for the ITS1 of *Penicillium crustosum*.

SEQ ID NO: 24 DNA sequence for the ITS2 of *Penicillium crustosum*.

SEQ ID NO: 25 DNA sequence for the ITS1 of *Penicillium expansum*.

SEQ ID NO: 26 DNA sequence for the ITS2 of *Penicillium expansum*.

SEQ ID NO: 27 DNA sequence for the ITS1 of *Hanseniaspora guilliermondii*.

SEQ ID NO: 28 DNA sequence for the ITS2 of *Hanseniaspora guilliermondii*.

SEQ ID NO: 29 DNA sequence for the ITS1 of *Debaryomyces carsonii*.

SEQ ID NO: 30 DNA sequence for the ITS2 of *Debaryomyces carsonii*.

SEQ ID NO: 31 DNA sequence for the ITS1 of *Pichia anomala*.

SEQ ID NO: 32 DNA sequence for the ITS2 of *Pichia anomala*.

SEQ ID NO: 33 DNA sequence for the ITS1 of *Pichia kluyveri*.

SEQ ID NO: 34 DNA sequence for the ITS2 of *Pichia kluyveri*.

SEQ ID NO: 35 DNA sequence for the ITS1 of *Candida krusei*.

SEQ ID NO: 36 DNA sequence for the ITS2 of *Candida krusei*.

SEQ ID NO: 37 Oligonucleotide Sequence SXUITS1a.
SEQ ID NO: 38 Oligonucleotide Sequence SXLITS2a.
SEQ ID NO: 39 Oligonucleotide Sequence SXUITS1b.
SEQ ID NO: 40 Oligonucleotide Sequence SXLITS2b.
SEQ ID NO: 41 Oligonucleotide Sequence SLUITS1a.
SEQ ID NO: 42 Oligonucleotide Sequence SLLITS2a.
SEQ ID NO: 43 Oligonucleotide Sequence SLUITS1b.
SEQ ID NO: 44 Oligonucleotide Sequence SLLITS2b.
SEQ ID NO: 45 Oligonucleotide Sequence BRUITS1a.
SEQ ID NO: 46 Oligonucleotide Sequence BRLITS2a.
SEQ ID NO: 47 Oligonucleotide Sequence BRUITS1b.
SEQ ID NO: 48 Oligonucleotide Sequence BRLITS2b.
SEQ ID NO: 49 Oligonucleotide Sequence BCUITS1a.
SEQ ID NO: 50 Oligonucleotide Sequence BCLITS2.
SEQ ID NO: 51 Oligonucleotide Sequence BCUITS1b.
SEQ ID NO: 52 Oligonucleotide Sequence PXUITS1a.
SEQ ID NO: 53 Oligonucleotide Sequence PXLITS2a.
SEQ ID NO: 54 Oligonucleotide Sequence PXUITS1b.

SEQ ID NO: 55 Oligonucleotide Sequence PXLITS2b.
SEQ ID NO: 56 Oligonucleotide Sequence HGUITS1.
SEQ ID NO: 57 Oligonucleotide Sequence HGLITS2.
SEQ ID NO: 58 Oligonucleotide Sequence DXLITS2a.
SEQ ID NO: 59 Oligonucleotide Sequence DXLITS2b.
SEQ ID NO: 60 Oligonucleotide Sequence PAUITS1.
SEQ ID NO: 61 Oligonucleotide Sequence PALITS2.
SEQ ID NO: 62 Oligonucleotide Sequence PKLITS2.
SEQ ID NO: 63 Oligonucleotide Sequence CKUITS1.
SEQ ID NO: 64 Oligonucleotide Sequence CKLITS2.
SEQ ID NO: 65 Oligonucleotide Sequence SXU99.
SEQ ID NO: 66 Oligonucleotide Sequence SXL658.
SEQ ID NO: 67 Oligonucleotide Sequence SXU102.
SEQ ID NO: 68 Oligonucleotide Sequence SXL661.
SEQ ID NO: 69 Oligonucleotide Sequence SLU85.
SEQ ID NO: 70 Oligonucleotide Sequence SLL635.
SEQ ID NO: 71 Oligonucleotide Sequence SLU88.
SEQ ID NO: 72 Oligonucleotide Sequence SLL636.
SEQ ID NO: 73 Oligonucleotide Sequence SLU136.
SEQ ID NO: 74 Oligonucleotide Sequence SLL634.
SEQ ID NO: 75 Oligonucleotide Sequence BRU53A.
SEQ ID NO: 76 Oligonucleotide Sequence BRU53B.
SEQ ID NO: 77 Oligonucleotide Sequence BRU77.
SEQ ID NO: 78 Oligonucleotide Sequence BRL339.
SEQ ID NO: 79 Oligonucleotide Sequence BRL367.
SEQ ID NO: 80 Oligonucleotide Sequence BRL390.
SEQ ID NO: 81 Oligonucleotide Sequence BCU136.
SEQ ID NO: 82 Oligonucleotide Sequence BCL393.
SEQ ID NO: 83 Oligonucleotide Sequence BCU142.
SEQ ID NO: 84 Oligonucleotide Sequence PXU87.
SEQ ID NO: 85 Oligonucleotide Sequence PXL495.
SEQ ID NO: 86 Oligonucleotide Sequence PXU86.
SEQ ID NO: 87 Oligonucleotide Sequence PXL482.
SEQ ID NO: 88 Oligonucleotide Sequence PXL491.
SEQ ID NO: 89 Oligonucleotide Sequence HGU193.
SEQ ID NO: 90 Oligonucleotide Sequence HGU231.
SEQ ID NO: 91 Oligonucleotide Sequence HGL601.
SEQ ID NO: 92 Oligonucleotide Sequence DXL447.
SEQ ID NO: 93 Oligonucleotide Sequence DXL526.
SEQ ID NO: 94 Oligonucleotide Sequence PAU133.
SEQ ID NO: 95 Oligonucleotide Sequence PAL451.
SEQ ID NO: 96 Oligonucleotide Sequence PKL356.
SEQ ID NO: 97 Oligonucleotide Sequence CKU104.
SEQ ID NO: 98 Oligonucleotide Sequence CKL354.
SEQ ID NO: 99 Oligonucleotide Sequence ITS5.
SEQ ID NO: 100 Oligonucleotide Sequence ITS4.

DETAILED DESCRIPTION OF THE INVENTION

The present invention provides unique DNA sequences which are useful in identifying fermentation-related microorganisms. These unique DNA sequences can be used as primers in PCR-based analysis for the identification of fermentation-related microorganisms, or as molecular probes to detect the presence of DNA from fermentation-related microorganisms. The DNA sequences of the present invention include the internal transcribed spacer (ITS) of the ribosomal RNA gene regions of specific fermentation-related microorganisms, as well as primers that are derived from these regions which are capable of identifying the particular microorganism.

The DNA sequences of the invention are from the ITS of the ribosomal RNA gene region of fermentation-related microorganisms. However, the present invention is not limited to detecting the presence of the microorganisms in fermentation operations, i.e., the invention can be used to detect the presence of such microorganisms from any source. There is variability in the ITS DNA sequences from different microorganisms. The ITS sequences can be aligned and compared. Primers can be designed based on regions within the ITS regions that contain the greatest differences in sequence among the fermentation-related microorganisms. The sequences and primers based on these sequences can be used to identify specific microorganisms.

DNA sequences of particular interest include ITS DNA sequences from Saccharomyces sp., especially *Saccharomyces cerevisiae* and *Saccharomyces bayanus;* Saccharomycodes sp., especially *Saccharomycodes ludwigii;* Dekkera sp., especially *Dekkera bruxellensis* and *Dekkera intermedia;* Botrytis sp., especially *Botrytis cinerea;* Penicillium sp., especially *Penicillium crustosum* and *Penicillium expansum;* Hanseniaspora sp., especially *Hanseniaspora guilliermondii;* Debaryomyces sp., especially *Debaryomyces carsonii;* Pichia sp., especially *Pichia anomala* and *Pichia kluyveri;* and Candida sp., especially *Candida krusei.* The ITS DNA sequences, as well as primers of interest, are set forth in SEQUENCE ID NOS: 1–100. The sequences are useful in PCR-based identification of fermentation-related microorganisms.

Methods for use of the primer sequences of the invention in PCR analysis are well known in the art. For example, see U.S. Pat. Nos. 4,683,195; 4,683,202 and 5,585,238, the contents of all of which are hereby incorporated by reference.

The primer sequences of the invention can also be used as molecular probes to detect the presence of target DNA. The Tm for the primers ranges from about 48–58° C. at 50 mM salt. The hybridization temperature is approximately 5–10° C. below the melting temperature. Thus, the primers are hybridized to target DNA typically at a temperature ranging from about 43–55° C. Final wash conditions generally range from about 45–55° C. at about 36 mM salt concentration. Specific hybridization as used herein means the use of a final high stringency wash in about 0.2X SSPE (salt concentration of about 36 mM) at a temperature appropriate for the particular primer. 1X SSPE contains 10 mM $NaH_2PO_4$, 180 mM NaCl, and 1 mM EDTA, at pH 7.4.

The ITS DNA sequences of the present invention can be cloned from fermentation-related microorganisms by methods known in the art. In general, the methods for the isolation of DNA from microorganism isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications,* Innes et al. (Eds.); pages 282–287; the contents of all of which are hereby incorporated by reference.

Alternatively, the ITS regions of interest can be identified by PCR amplification. Primers to amplify the entire ITS region can be synthesized according to White et al. (1990; In PCR Protocols; Eds.: Innes et al., pages 315–322, the contents of which are hereby incorporated by reference).

The ITS sequences were determined and the sequences were compared to locate divergences which might be useful to test in PCR to distinguish the different fermentation-related microorganisms. The sequences of the ITS regions which were determined are shown as Sequence ID NOS: 1 to 12. The DNA sequences for the ITS1 and ITS2 regions are shown as Sequence ID NOS: 13 to 36. From the identification of divergences, numerous primers were synthesized and tested in PCR-amplification. Purified microorganism DNA and DNA isolated from fermentation cultures and colonies were used as templates for PCR-amplification. Thus, pairs of diagnostic primers were identified, i.e., those which identified one particular fermentation-related microorganism species. Preferred primer combinations are able to distinguish between the different microorganisms in, for example, fermentation cultures. Primer sequences are set forth in Sequence ID NOS: 65 to 98, with flanking sequences depicted in Sequence ID NOS: 37 to 64. Thus, while oligonucleotide primers selected from among Sequence ID NOS: 65 to 98 are preferred, primers may also be used which contain at least 10 contiguous-nucleotide bases from one of SEQ ID NOS: 65 to 98. Additionally, primers may be used which contain at least 10 contiguous nucleotide bases from one of SEQ ID NOS: 65 to 98 contiguous with 1 to 15 nucleotide bases in the 5' and/or 3' direction of corresponding SEQ ID NOS: 37 to 64, and primers of 10 nucleotide bases or longer which contain at least 5 contiguous nucleotide bases from one of SEQ ID NOS: 65 to 98 contiguous with from 1 to 15 nucleotide bases in the 5' and/or 3' direction of corresponding SEQ ID NOS: 37 to 64.

The present invention provides numerous diagnostic primer combinations. The primers of the invention are designed based on sequence differences among the microorganism ITS regions. A minimum of one base pair difference between sequences can permit design of a discriminatory primer. In general, primers should have a theoretical melting temperature between about 55° C. to about 65° C. to achieve good sensitivity, and should be void of significant secondary structure and 3' overlaps between primer combinations. Primers are generally at least about 10 nucleotide bases, more preferably at least about 15 to about 20 nucleotide bases.

The oligonucleotide primers of the present invention are particularly useful in detecting microorganisms involved in fermentations, in particular, microorganisms selected from among *Saccharomyces cerevisiae, Saccharomyces bayanus, Saccharomycodes ludwigii, Dekkera bruxellensis, Dekkera intermedia, Botrytis cinerea, Penicillium crustosum, Penicillium expansum, Hanseniaspora guilliermondii, Debaryomyces carsonii, Pichia anomala, Pichia kluyveri,* and *Candida krusei*. However, the primers of the present invention can also be used to detect the presence of the foregoing microorganisms from any source.

The present invention also relates to the preparation of "kits" containing elements for detecting fermentation-related microorganisms. Such a kit may comprise a carrier to receive therein one or more containers, such as tubes or vials. Unlabeled or detectably labeled oligonucleotide primers may be contained in one or more of the containers. The oligonucleotide primers may be present in lyophilized form, or in an appropriate buffer. One or more enzymes or reagents for use in PCR reactions may be contained in one or more of the containers. The enzymes or reagents may be present alone or in admixture, and in lyophilized form or in appropriate buffers. The kit may also contain any other component necessary for carrying out the present invention, such as buffers, extraction agents, enzymes, pipettes, plates, nucleic acids, nucleoside triphosphates, filter paper, gel materials, transfer materials, and autoradiography supplies.

The examples below illustrate typical experimental protocols which can be used in the isolation of ITS sequences, the selection of suitable primer sequences, the testing of primers for selective and diagnostic efficacy, and the use of such primers to detect the presence of a fermentation-related microorganism. Such examples are provided by way of illustration and not by way of limitation.

EXAMPLES

Example 1

Culture of Yeast and Fungal Isolates

Viable isolates of *Botrytis cinerea, Penicillium crustosum,* and *Penicillium expansum* were obtained from the American Type Culture Collection (ATCC). Fungi ere grown in 40 ml of Malt Yeast Extract Broth in 250 ml flasks inoculated with mycelial fragments from two-week-old cultures grown on Malt Yeast Extract Agar (MYEA). Liquid cultures were incubated at room temperature for 14 days without shaking. Malt Yeast Extract Agar plates were inoculated with mycelia and grown for 2 weeks. Viable isolates of *Saccharomyces cerevisiae, Saccharomyces bayanus, Saccharomycodes ludwigii, Dekkera bruxellensis, Dekkera intermedia, Dekkera anomala, Hanseniaspora guilliermondii, Debaryomyces carsonii, Pichia anomala, Pichia kluyveri,* and *Candida krusei* were obtained from the ATCC or from the Gallo Sonoma Winery (see Table 1). Yeasts were grown on any of several media of choice.

Example 2

Amplification and Sequencing of the Internal Transcribed Spacer (ITS) Regions

The internal transcribed spacer region was amplified from the different isolates directly from the fungal mycelium or the yeast colony using ITS5 (5'-GGAAGTAAAAGTCGTAACAAGG-3'; SEQ ID NO: 99) and ITS4 (5'-TCCTCCGCTTATTGATATGC-3'; SEQ ID NO: 100). A sterile pipette tip was used to scrape a small amount of mycelia or colony off of the plate and deposited into a 250-µl microcentrifuge tube containing 5 µl each of GeneAmp®10X PCR Buffer II and MgCl$_2$ solution (PE Applied Biosystems, Foster City, Calif.; part no. N808-0161), 0.2 mM each of dATP, dCTP, dGTP, and dTTP (GeneAmp® dNTPs; PE Applied Biosystems, Foster City, Calif.; part no. N808-0007), approximately 25 pmole/µl each of ITS5 and ITS4, and 2.5 Units AmpliTaq® DNA polymerase (PE Applied Biosystems; part no. N808-0161). Reactions were run for 35 cycles of 30 s at 94° C., 40 s at 58° C., and 2 min at 72° C., followed by a final elongation step at 72° C. for 10 min, on a Perkin Elmer GeneAmp® PCR System 9600 (PE Applied Biosystems). PCR products were purified using QIAquick® PCR Purification Kits (Qiagen Inc., Santa Clarita, Calif.) to remove any excess primers, nucleotides, and polymerases. Five microliters of the purified PCR products were run on a 1.2% agarose gel with 5 µl of pGEM-3Zf(+) double-stranded DNA Control Template (0.2 g/L, PE Applied Biosystems) to approximate concentrations. All products were sequenced using the primers ITS5 and ITS4 (see sequences above; White et al., 1990; In: *PCR Protocols;* Eds.: Innes et al. pp. 315–322). Sequencing was performed on an PE Applied Biosystems 377 Automated DNA Sequencer® using ABI PRISM™ Dye Terminator Cycle Sequencing Ready Reaction Kits® (PE Applied Biosystems; part no. 402079). Cycle sequencing products were run over Centri-Sep® spin columns (Princeton Separations, Inc., Adelphia, N.J.) to remove excess primers, dye-labeled terminators, nucleotides, and polymerases before being run on the automated sequencer.

Example 3

Selection of Species-Specific Primers

The ITS sequences of the *Saccharomyces cerevisiae, Saccharomyces bayanus, Saccharomycodes ludwigii, Dekkera bruxellensis, Dekkera intermedia, Dekkera anomala, Botrytis cinerea, Penicillium crustosum, Penicillium expansum, Hanseniaspora guilliermondii, Debaryomyces carsonii, Pichia anomala, Pichia kluyveri,* and *Candida krusei* isolates were aligned and primers were designed using Oligo 5.0 (National Biosciences, Inc., Plymouth, Minn.) in regions of maximum sequence difference between the target species.

Example 4

Primer Synthesis

Primers were synthesized on an Applied Biosystems 394 DNA/RNA Synthesizer® using phosphoramidite chemistry.

Example 5

Verification of Primer Specificity to Target Species

Different annealing temperatures were tested to determine the optimal temperature for PCR for individual primers. In cases with multiple species-specific primers, different primer combinations were used to determine the best primer combination and annealing temperature to amplify a single species-specific DNA fragment. Species-specific amplification products were produced from primers designed from the ITS region between the 18S and 28S ribosomal DNA subunits of each fungal strain of interest.

Example 6

Utilization of ITS Sequences as Diagnostic Probes to Hybridize With Target DNA 1. Put chosen concentration of DNA sample in 100 ul of TE, pH 7.0.

2. Add 0.1 volume [10 µl] of 3.0 M NaOH, vortex to mix and incubate at 65° C. for 20 min to destroy the RNA and denature the DNA.

3. Spin down condensation. Allow samples to cool to room temp. Neutralize by adding 1.0 volume [110 µl] of 2M ammonium acetate, pH 7.0, vortex to mix. Spin down to remove solution off of cap. Refrigerate until slot blot apparatus is ready.

4. Apply to slot-blot apparatus according to manufacturers protocol; about 220 µl to slot blot.

5. Label ITS sequence probe according to kit manufacturer's recommendation.

6. Prehybridize blots in 1.0% BSA; 1 mM EDTA, 0.5 M NaHPO$_4$, pH 7.2, 7.0% sodium dodecyl sulfate for a minimum of 2 hr prior to adding the probe, and then hybridized for 16 hr at 45° C. Initial washes consist of two 30-min washes in 1X SSPE/0.1% SDS at 50° C. Transfer blots to a plastic tray and wash in 1X SSPE for 1 hr, at 50° C. with shaking. The final wash should consist of 15 min at 50° C. in 0.2X SSPE.

While the invention has been described in detail and with reference to specific embodiments thereof, it will be apparent to one skilled in the art that various changes and modifications can be made therein without departing from the spirit and scope thereof.

TABLE 1

Sources of test isolates

| Species name | ID number | Source |
| --- | --- | --- |
| Saccharomyces cerevisiae | GS061 | Gallo of Sonoma[1] |
| Saccharomyces cerevisiae | GS117 | Gallo of Sonoma |
| Saccharomyces cerevisiae | 4127 | ATCC[2] |
| Saccharomyces bayanus | 13056 | ATCC |
| Saccharomycodes ludwigii | 34085 | ATCC |
| Saccharomycodes ludwigii | 44299 | ATCC |
| Dekkera bruxellensis | Y153 | Gallo of Sonoma |
| Dekkera bruxellensis | Y207 | Gallo of Sonoma |
| Dekkera bruxellensis | 10560 | ATCC |
| Dekkera intermedia | 34448 | ATCC |
| Dekkera anomala | 10559 | ATCC |
| Botrytis cinerea | 20599 | ATCC |
| Penicillium crustosum | 58616 | ATCC |
| Penicillium expansum | 28885 | ATCC |
| Hanseniaspora guilliermondii | GS014 | Gallo of Sonoma |
| Hanseniaspora guilliermondii | GS057 | Gallo of Sonoma |
| Hanseniaspora guilliermondii | 66166 | ATCC |
| Debaryomyces carsonii | Y443 | Gallo of Sonoma |
| Debaryomyces carsonii | Y448 | Gallo of Sonoma |
| Debaryomyces carsonii | 24214 | ATCC |
| Pichia anomala | GS085 | Gallo of Sonoma |
| Pichia anomala | 34080 | ATCC |
| Pichia kluyveri | GS070 | Gallo of Sonoma |
| Pichia kluyveri | 64303 | ATCC |
| Candida krusei | GS076 | Gallo of Sonoma |
| Candida krusei | GS096 | Gallo of Sonoma |
| Candida krusei | GS108 | Gallo of Sonoma |

[1]Gallo of Sonoma Winery, Healdsburg, CA, USA
[2]American Type Culture Collection, Rockville, MD, USA

TABLE 2

| Target Organism | Primer Name | Primer Sequence |
| --- | --- | --- |
| Saccharomyces sp. | SXU99 | 5'-CTTTTACTGGGCAAGAAGAC-3' (SEQ ID NO: 65) |
| Saccharomyces sp. | SXL658 | 5'-AAGCACGCAGAGAAACC-3' (SEQ ID NO: 66) |
| Saccharomyces sp. | SXU102 | 5'-TTACTGGGCAAGAAGACAAG-3' (SEQ ID NO: 67) |
| Saccharomyces sp. | SXL661 | 5'-CTCAAGCACGCAGAGAA-3' (SEQ ID NO: 68) |
| Saccharomycodes ludwigii | SLU85 | 5'-GACTTTTCTTGGGGAGAG-3' (SEQ ID NO: 69) |
| Saccharomycodes ludwigii | SLL635 | 5'-TCACTAGTTGGGATAAACCT-3' (SEQ ID NO: 70) |
| Saccharomycodes ludwigii | SLU88 | 5'-TTTTCTTGGGGAGAGG-3' (SEQ ID NO: 71) |
| Saccharomycodes ludwigii | SLL636 | 5'-ATCACTAGTTGGGATAAACC-3' (SEQ ID NO: 72) |
| Saccharomycodes ludwigii | SLU136 | 5'-CGGCTAGTAGTTGATGATT-3' (SEQ ID NO: 73) |
| Saccharomycodes ludwigii | SLL634 | 5'-CACTAGTTGGGATAAACCTA-3' (SEQ ID NO: 74) |
| Dekkera sp | BRU53A | 5'-ATTACAGGATGCTGGGC-3' (SEQ ID NO: 75) |
| Dekkera sp. | BRU53B | 5'-ATTACAGGATGCTGGG-3' (SEQ ID NO: 76) |
| Dekkera sp. | BRU77 | 5'-CGTGCAGACACGTGGAT-3' (SEQ ID NO: 77) |
| Dekkera sp. | BRL339 | 5'-CTTTGAAGAAAACACCCTC-3' (SEQ ID NO: 78) |
| Dekkera sp. | BRL367 | 5'-AATCATTATCCCCTCACTC-3' (SEQ ID NO: 79) |
| Dekkera sp. | BRL390 | 5'-TAATGAACGGCCGAAAC-3' (SEQ ID NO: 80) |
| Botrytis cinerea | BCU136 | 5'-TTGTATGCTCGCCAGAG-3' (SEQ ID NO: 81) |

TABLE 2-continued

| Target Organism | Primer Name | Primer Sequence |
|---|---|---|
| Botrytis cinerea | BCL393 | 5'-GCCTGCCATTACTGACA-3' (SEQ ID NO: 82) |
| Botrytis cinerea | BCU142 | 5'-GCTCGCCAGAGAATACC-3' (SEQ ID NO: 83) |
| Penicillium sp. | PXU87 | 5'-ACCCGTGTTTATTTTACCTT-3' (SEQ ID NO: 84) |
| Penicillium sp. | PXL495 | 5'-CTACAGAGCGGGTGACA-31 (SEQ ID NO: 85) |
| Penicillium sp. | PXU86 | 5'-CACCCGTGTTTATTTTACCT-3' (SEQ ID NO: 86) |
| Penicillium sp. | PXL482 | 5'-CAAAGCCCCATACGC-3' (SEQ ID NO: 87) |
| Penicillium sp. | PXL491 | 5'-AGCGGGTGACAAAGC-3' (SEQ ID NO: 88) |
| Hanseniaspora guilliermondii | HGU193 | 5'-CAACGTTACACACATTGG-3' (SEQ ID NO: 89) |
| Hanseniaspora guilliermondii | HGU231 | 5'-AATTCTTTCTGCTTTGAATCG-3' (SEQ ID NO: 90) |
| Hanseniaspora guilliermondii | HGL601 | 5'-CAGCGTCTCCAAAGAAGCTAA-3' (SEQ ID NO: 91) |
| Debaryomyces carsonii | DXL447 | 5'-GCAAACGCCTAGTTCGACTAA-3' (SEQ ID NO: 92) |
| Debaryomyces carsonii | DXL526 | 5'-ATTCAACGAGTTGGATAAACC-3' (SEQ ID NO: 93) |
| Pichia anomala | PAU133 | 5'-GGCTTACTGCCCAAAGGTC-3' (SEQ ID NO: 94) |
| Pichia anomala | PAL451 | 5'-TGCTTATTAGTACACTCTTGC-3' (SEQ ID NO: 95) |
| Pichia kluyveri | PKL356 | 5'-GTTTAGTTCACTTCGTCCACG-3' (SEQ ID NO: 96) |
| Candida krusei | CKU104 | 5'-CCTAAAATGTGGAATATAGCA-3' (SEQ ID NO: 97) |
| Candida krusei | CKL354 | 5'-ACGCTCTTTACACGTCGTC-3' (SEQ ID NO: 98) |

TABLE 3

ITS-derived Diagnostic PCR Primers

| Target Organism | 5' Primer | 3' Primer | Approximate Size of PCR Product (bp) |
|---|---|---|---|
| Saccharomyces sp. | SXU99 | ITS4 | 750 |
| Saccharomyces sp. | SXU102 | ITS4 | 750 |
| Saccharomyces sp. | ITS5 | SXL658 | 695 |
| Saccharomyces sp. | ITS5 | SXL661 | 695 |
| Saccharomyces sp. | SXU99 | SXL658 | 560 |
| Saccharomyces sp. | SXU99 | SXL661 | 560 |
| Saccharomyces sp. | SXU102 | SXL658 | 560 |
| Saccharomyces sp. | SXU102 | SXL661 | 560 |
| Saccharomycodes ludwigii | SLU85 | ITS4 | 660 |
| Saccharomycodes ludwigii | SLU88 | ITS5 | 660 |
| Saccharomycodes ludwigii | SLU136 | ITS4 | 610 |
| Saccharomycodes ludwigii | ITS5 | SLL635 | 670 |
| Saccharomycodes ludwigii | ITS5 | SLL636 | 670 |
| Saccharomycodes ludwigii | ITS5 | SLL634 | 670 |
| Saccharomycodes ludwigii | SLU85 | SLL635 | 565 |
| Saccharomycodes ludwigii | SLU85 | SLL636 | 565 |
| Saccharomycodes ludwigii | SLU85 | SLL634 | 565 |
| Saccharomycodes ludwigii | SLU88 | SLL635 | 565 |
| Saccharomycodes ludwigii | SLU88 | SLL636 | 565 |
| Saccharomycodes ludwigii | SLU88 | SLL634 | 565 |
| Saccharomycodes ludwigii | SLU136 | SLL635 | 500 |
| Saccharomycodes ludwigii | SLU136 | SLL636 | 500 |
| Saccharomycodes ludwigii | SLU136 | SLL634 | 500 |
| Dekkera sp. | BRU53A | ITS4 | 450 |
| Dekkera sp. | BRU53B | ITS4 | 450 |
| Dekkera sp. | BRU77 | ITS4 | 450 |

TABLE 3-continued

ITS-derived Diagnostic PCR Primers

| Target Organism | 5' Primer | 3' Primer | Approximate Size of PCR Product (bp) |
|---|---|---|---|
| Dekkera sp. | ITS5 | BRL339 | 375 |
| Dekkera bruxellensis | ITS5 | BRL367 | 400 |
| Dekkera sp. | ITS5 | BRL390 | 425 |
| Dekkera sp. | BRU53A | BRL339 | 290 |
| Dekkera bruxellensis | BRU53A | BRL367 | 320 |
| Dekkera sp. | BRU53A | BRL390 | 340 |
| Dekkera sp. | BRU53B | BRL339 | 290 |
| Dekkera bruxellensis | BRU53B | BRL367 | 320 |
| Dekkera sp. | BRU53B | BRL390 | 340 |
| Dekkera sp. | BRU77 | BRL339 | 260 |
| Dekkera bruxellensis | BRU77 | BRL367 | 290 |
| Dekkera sp. | BRU77 | BRL390 | 310 |
| Botrytis cinerea | BCU136 | ITS4 | 350 |
| Botrytis cinerea | BCU142 | ITS4 | 345 |
| Botrytis cinerea | ITS5 | BCL393 | 420 |
| Botrytis cinerea | BCU136 | BCL393 | 270 |
| Botrytis cinerea | BCU142 | BCL393 | 265 |
| Penicillium sp. | PXU87 | ITS4 | 410 |
| Penicillium sp. | PXU86 | ITS4 | 410 |
| Penicillium sp. | ITS5 | PXL495 | 530 |
| Penicillium sp. | ITS5 | PXL482 | 520 |
| Penicillium sp. | ITS5 | PXL491 | 530 |
| Penicillium sp. | PXU87 | PXL495 | 405 |
| Penicillium sp. | PXU87 | PXL482 | 395 |
| Penicillium sp. | PXU87 | PXL491 | 405 |
| Hanseniaspora guilliermondii | HGU193 | ITS4 | 530 |
| Hanseniaspora guilliermondii | HGU231 | ITS4 | 490 |
| Hanseniaspora guilliermondii | ITS5 | HGL601 | 630 |
| Hanseniaspora guilliermondii | HGU193 | HGL601 | 420 |
| Hanseniaspora guilliermondii | HGU231 | HGL601 | 380 |
| Debaryomyces carsonii | ITS5 | DXL447 | 480 |
| Debaryomyces carsonii | ITS5 | DXL526 | 560 |
| Pichia anomala | PAU133 | ITS4 | 505 |
| Pichia anomala | ITS5 | PAL451 | 480 |
| Pichia anomala | PAU133 | PAL451 | 320 |
| Pichia kluyveri | ITS5 | PKL356 | 390 |
| Candida krusei | CKU104 | ITS4 | 440 |
| Candida krusei | ITS5 | CKL354 | 385 |

We claim:

1. An isolated double stranded nucleic acid which consists of a member selected from the group consisting of SEQ ID NOS: 13 to 20 and 25 to 34 and its complementary sequence.

2. An isolated nucleic acid which specifically hybridizes with a nucleic acid selected from the group consisting of SEQ ID NOS: 15 to 20 and 25 to 34, and their complementary sequences.

3. An oligonucleotide sequence for identification of a fermentation-related microorganism, wherein said sequence is selected from the group consisting of SEQ ID NOS: 37 to 64.

4. An oligonucleotide primer which is a fragment of the sequences according to claim 3, and which specifically hybridizes to the ITS1 or ITS2 of *Saccharomyces cerevisiae, Saccharomyces bayanus, Saccharomycodes ludwigii, Dekkera bruxellensis, Dekkera intermedia, Botrytis cinerea, Penicillium crustosum, Penicillium expansum, Hanseniaspora guilliermondii, Debaryomyces carsonii, Pichia anomala, Pichia kluyveri* or *Candida krusei.*

5. An oligonucleotide primer for identification of a fermentation-related microorganism, wherein said primer specifically amplifies at least a portion of the ITS1 region of SEQ ID NOS: 13, 15, 17, 19, 21, 23, 25, 27, 29, 31, 33 or 35 or at least a portion of the ITS2 region of SEQ ID NOS: 14, 16, 18, 20, 22, 24, 26, 28, 30, 32, 34 or 36, or which specifically amplifies at least a portion of the ITS region of a fermentation-related microorganism selected from the group consisting of Saccharomyces sp., Saccharomycodes sp., Debkera sp., Botrytis sp., Penicillium sp., Hanseniaspora sp., Debaryomyces sp., Pichia sp. and Candida sp., wherein said primer is selected from the group consisting of primers which contain at least 10 contiguous bases from one of SEQ ID NOS: 65 to 98, primers which contain which contain at least 10 contiguous bases from one of SEQ ID NOS: 65 to 98 contiguous with 1 to 15 flanking nucleotide bases in the 5' and/or 3' direction of SEQ ID NOS: 37 to 64, and primers of 10 nucleotide bases or longer which contain at least 5 contiguous nucleotide bases from one of SEQ ID NOS: 65 to 98 contiguous with from 1 to 15 flanking nucleotide bases in the 5' and/or 3' direction of SEQ ID NOS: 37 to 64 wherein said primer specifically amplifies at least a portion of the ITS region of members of a specific species of fermentation-related microorganism but does not amplify the ITS regions of other species of fermentation-related microorganisms.

6. A pair of oligonucleotide primers for use in the amplification-based detection of an internal transcribed spacer sequence of a fermentation-related microorganism, wherein said primers specifically amplify at least a portion of the ITS1 region of SEQ ID NOS: 13, 15, 17, 19, 21, 23, 25, 27, 29, 31, 33 or 35 or at least a portion of the ITS2 region of SEQ ID NOS: 14, 16, 18, 20, 22, 24, 26, 28, 30, 32, 34 or 36, or which specifically amplify at least a portion of the ITS region of a fermentation-related microorganism selected from the group consisting of Saccharomyces sp., Saccharomycodes sp., Dekkera sp., Botrytis sp., Penicillium sp., Hanseniaspora sp., Debaryomyces sp., Pichia sp. and Candida sp., wherein said primers are selected from the group consisting of primers which contain at least 10 contiguous nucleotide bases from one of SEQ ID NOS: 65 to 98, primers which contain at least 10 contiguous nucleotide bases from one of SEQ ID NOS: 65 to 98 contiguous with 1 to 15 flanking nucleotide bases in the 5' and/or 3' direction of SEQ ID NOS: 37 to 64, and primers of 10 bases or longer which contain at least 5 contiguous nucleotide bases from one of SEQ ID NOS: 65 to 98 contiguous with 1 to 15 nucleotide flanking bases in the 5' and/or 3' direction of SEQ ID NOS: 37 to 64 wherein said primers specifically amplify at least a portion of the ITS region of members of a specific species of fermentation-related microorganism but do not amplify the ITS regions of other species of fermentation-related microorganisms.

7. The pair of oligonucleotide primers according to claim 6 which comprises SEQ ID NO: 65 and SEQ ID NO: 66.

8. The pair of oligonucleotide primers according to claim 6 which comprises SEQ ID NO: 67 and SEQ ID NO: 68.

9. The pair of oligonucleotide primers according to claim 6 which comprises SEQ ID NO: 69 and SEQ ID NO: 70.

10. The pair of oligonucleotide primers according to claim 6 which comprises SEQ ID NO: 71 and SEQ ID NO: 72.

11. The pair of oligonucleotide primers according to claim 6 which comprises SEQ ID NO: 73 and SEQ ID NO: 74.

12. The pair of oligonucleotide primers according to claim 6 which comprises SEQ ID NO: 75 and SEQ ID NO: 78.

13. The pair of oligonucleotide primers according to claim 6 which comprises SEQ ID NO: 76 and SEQ ID NO: 79.

14. The pair of oligonucleotide primers according to claim 6 which comprises SEQ ID NO: 77 and SEQ ID NO: 80.

15. The pair of oligonucleotide primers according to claim 6 which comprises SEQ ID NO: 81 and SEQ ID NO: 82.

16. The pair of oligonucleotide primers according to claim 6 which comprises SEQ ID NO: 82 and SEQ ID NO: 83.

17. The pair of oligonucleotide primers according to claim 6 which comprises SEQ ID NO: 84 and SEQ ID NO: 85.

18. The pair oligonucleotide primers according to claim 6 which comprises SEQ ID NO: 86 and SEQ ID NO: 87.

19. The pair of oligonucleotide primers according to claim 6 which comprises SEQ ID NO: 86 and SEQ ID NO: 88.

20. The pair of oligonucleotide primers according to claim 6 which comprises SEQ ID NO: 89 and SEQ ID NO: 91.

21. The pair of oligonucleotide primers according to claim 6 which comprises SEQ ID NO: 90 and SEQ ID NO: 91.

22. The pair oligonucleotide primers according to claim 6 which comprises SEQ ID NO: 94 and SEQ ID NO: 95.

23. The pair of oligonucleotide primers according to claim 6 which comprises SEQ ID NO: 97 and SEQ ID NO: 98.

24. A method for detection of a fermentation-related microorganism comprising:
  (a) obtaining DNA from a fungal culture or colony isolated from a fermentation, or from an organism present in a fermentation beverage;
  (b) amplifying a part of the internal transcribed spacer sequence of said fermentation-related microorganism using said DNA as a template in a polymerase chain reaction with a pair of oligonucleotide primers according to claim 6; and
  (c) visualizing said amplified part of the internal transcribed spacer sequence to determine whether said fermentation-related microorganism is present.

25. The method according to claim 24, wherein said fermentation-related microorganism is selected from the group consisting of *Saccharomyces cerevisiae, Saccharomyces bayanus, Saccharomycodes ludwigii, Dekkera bruxellensis, Dekkera intermedia, Botrytis cinerea, Penicillium crustosum, Penicillium expansum, Hanseniaspora guilliermondii, Debaryomyces carsonii, Pichia anomala, Pichia kluyveri,* and *Candida krusei.*

26. The method according to claim 24, wherein said fungal culture is isolated from a wine fermentation or said fermentation beverage is a wine fermentation beverage.

27. The method according to claim 24, wherein the pair of oligonucleotide primers comprises SEQ ID NO: 65 and SEQ ID NO: 66.

28. The method according to claim 24, wherein the pair of oligonucleotide primers comprises SEQ ID NO: 67 and SEQ ID NO: 68.

29. The method according to claim 24, wherein the pair of oligonucleotide primers comprises SEQ ID NO: 69 and SEQ ID NO: 70.

30. The method according to claim 24, wherein the pair of oligonucleotide primers comprises SEQ ID NO: 71 and SEQ ID NO: 72.

31. The method according to claim 24, wherein the pair of oligonucleotide primers comprises SEQ ID NO: 73 and SEQ ID NO: 74.

32. The method according to claim 24, wherein the pair of oligonucleotide primers comprises SEQ ID NO: 75 and SEQ ID NO: 78.

33. The method according to claim 24, wherein the pair of oligonucleotide primers comprises SEQ ID NO: 76 and SEQ ID NO: 79.

34. The method according to claim 24, wherein the pair of oligonucleotide primers comprises SEQ ID NO: 77 and SEQ ID NO: 80.

35. The method according to claim 24, wherein the pair of oligonucleotide primers comprises SEQ ID NO: 81 and SEQ ID NO: 82.

36. The method according to claim 24, wherein the pair of oligonucleotide primers comprises SEQ ID NO: 82 and SEQ ID NO: 83.

37. The method according to claim 24, wherein the pair of oligonucleotide primers comprises SEQ ID NO: 84 and SEQ ID NO: 85.

38. The method according to claim 24, wherein the pair of oligonucleotide primers comprises SEQ ID NO: 86 and SEQ ID NO: 87.

39. The method according to claim 24, wherein the pair of oligonucleotide primers comprises SEQ ID NO: 86 and SEQ ID NO: 88.

40. The method according to claim 24, wherein the pair of oligonucleotide primers comprises SEQ ID NO: 89 and SEQ ID NO: 91.

41. The method according to claim 24, wherein the pair of oligonucleotide primers comprises SEQ ID NO: 90 and SEQ ID NO: 91.

42. The method according to claim 24, wherein the pair of oligonucleotide primers comprises SEQ ID NO: 94 and SEQ ID NO: 95.

43. The method according to claim 24, wherein the pair of oligonucleotide primers comprises SEQ ID NO: 97 and SEQ ID NO: 98.

44. A kit comprising a carrier to receive therein one or more containers, at least one of said containers comprising an oligonucleotide primer according to claim 5.

45. A kit comprising a carrier to receive therein one or more containers, at least one of said containers comprising a pair of oligonucleotide primers according to claim 6.

* * * * *

UNITED STATES PATENT AND TRADEMARK OFFICE
CERTIFICATE OF CORRECTION

PATENT NO. : 6,248,519 B1
DATED : June 19, 2001
INVENTOR(S) : Engel et al.

It is certified that error appears in the above-identified patent and that said Letters Patent is hereby corrected as shown below:

Column 8,
Line 16, replace "ere" with -- were --.
Line 63, replace "on an PE" with -- on a PE --.

Column 9,
Line 43, replace "100 ul" with -- 100µl --.

Column 11,
Line 11, replace "31" with -- 3' --.
Line 48, under 3' Primer column replace "ITS5" with -- ITS4 --.

Column 59,
Line 55, replace "Debkera" with -- Dekkera --.
Lines 59-60, delete "which contain" (second occurrence).

Column 61,
Line 11, insert -- of -- after pair and before oligonucleotide.
Line 19, insert -- of -- after pair and before oligonucleotide.

Signed and Sealed this

Twenty-first Day of May, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 100

(2) INFORMATION FOR SEQ ID NO: 1:

(i) SEQUENCE CHARACTERISTICS:
       (A) LENGTH: 754 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 1:

```
AAGAAATTTA ATAATTTTGA AAATGGATTT TTTTGTTTTG GCAAGAGCAT GAGAGCTTTT      60

ACTGGGCAAG AAGACAAGAG ATGGAGAGTC CACCCGGGCC TGCGCTTAAG TGCGCGGTCT     120

TGCTAGGCTT GTAAGTTTCT TTCTTGCTAT TCCAAACGGT GAGAGATTTC TGTGCTTTTG     180

TTATAGGACA ATTAAAACCG TTTCAATACA ACACACTGTG GAGTTTTCAT ATCTTTGCAA     240

CTTTTTCTTT GGGCATTCGA GCAATCGGGG CCCAGAGGTA ACAAACACAA ACAATTTTAT     300

CTATTCATTA AATTTTTGTC AAAAACAAGA ATTTTCGTAA CTGGAAATTT TAAAATATTA     360

AAAACTTTCA ACAACGGATC TCTTGGTTCT CGCATCGATG AAGAACGCAG CGAAATGCGA     420

TACGTAATGT GAATTGCAGA ATTCCGTGAA TCATCGAATC TTTGAACGCA CATTGCGCCC     480

CTTGGTATTC CAGGGGGCAT GCCTGTTTGA GCGTCATTTC CTTCTCAAAC ATTCTGTTTG     540

GTAGTGAGTG ATACTCTTTG GAGTTAACTT GAAATTGCTG GCCTTTTCAT TGGATGTTTT     600

TTTTTCCAAA GAGAGGTTTC TCTGCGTGCT TGAGGTATAA TGCAAGTACG GTCGTTTTAG     660

GTTTTACCAA CTGCGGCTAA TCTTTTTTTA TACTGAGCGT ATTGGAACGT TATCGATAAG     720

AAGAGAGCGT CTAGGCGAAC AATGTTCTTA AAGT                                 754
```

(2) INFORMATION FOR SEQ ID NO: 2:

(i) SEQUENCE CHARACTERISTICS:
       (A) LENGTH: 657 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 2:

```
AAGAAAAAAA CTGTTTATAA ACAGACGGTA GACTTTTCTT GGGGAGAGGT TGTTGATTGC      60

TTTGGCCTGC GCTTAACTGC GCGGCTAGTA GTTGATGATT TTGTTATTAT CCGAGACGAA     120

GGAAACGTCT GATTTAAAA ACATTATACA CTTTGGAGTA CTTTTTTTAA TGTATTTCTT     180

CCTTGGACGA GCAATTGTTC AAGGGTCAAT AAACACAAAC AATTTTTTTT TTATTTAAAT     240

TTAAAATAAT TCAAAATATA TCATTTCTTT TATTAGGAAT ATAAAAATTT TAAAACTTTC     300

AACAACGGAT CTCTTGGTTC TCGCATCGAT GAAGAACGTA GCGAATTGCG ATAAGTAATG     360

TGAATTGCAG ATTTTCGTGA ATCATTGAAT TTTTGAACGC ACATTGCGCC CTTTGGTATT     420

CCAAAGGGCA TGCCTGTTTG AGCGTCATTT CCTTCTCAAA AGAGTTTTTT TATTCTTTTG     480

GTTGTGAGTG ATACTCTTTC CTTTTACAGG GAAGGGGTTA ACTTGAAATT GTTGCCTAGC     540

AAAGAAGAAT TTTGATTGAA ATTTCTTGTT TATTACTATT AGGTTTATCC CAACTAGTGA     600

TTATTGAGAG TTTTTATTAC AGAGTCTTTT CACTTGCTAT AATACTATTC TATAAGT       657
```

(2) INFORMATION FOR SEQ ID NO: 3:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
CAGGATGCTG GGCGCAAGCC CGTGCAGACA CGTGGATAAG CAAGGATAAA AATACATTAA      60
ATTTATTTAG TTTAGTCAAG AAAGAATTTT AAAACTTTCA ACAATGGATC TCTTGGTTCT     120
CGCGTCGATG AAGAGCGCAG CGGAATTGCG ATACTTAATG TGAATTGCAG ATTTTCGTGA     180
ATCATCGAGT TCTTGAACGC ACATTGCGCC CTCTGGTATT CCGGAGGGCA TGCCTGTTTG     240
AGCGTCATTT CCTTCTCACT ATTTAGTGGT TATGAGATTA CACGAGGGTG TTTTCTTCAA     300
AGGAAAGAGG GGAGAGTGAG GGGATAATGA TTTAAGGTTT CGGCCGTTCA TTATTTTTTT     360
CTTCTCCCCC AGTTATCAAG T                                               381
```

(2) INFORMATION FOR SEQ ID NO: 4:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CAGGATGCTG GGCGCAAGCC CGTGCAGACA CGTGGATAAG TAAGGATAAA AATACATTAA      60
ATTTATTTAG TTTTAGTCAA GAAAGAATTT TAAAACTTTC AACAATGGAT CTCTTGGTTC     120
TCGCGTCGAT GAAGAGCGCA GCGAATTGCG ATACTTAATG TGAATTGCAG ATTTTCGTGA     180
ATCATCGAGT TCTTGAACGC ACATTGCGCC CTCTGGTATT CCGGAGGGCA TGCCTGTTTG     240
AGCGTCATTT CCTTCTCACT ATTTAGTGGT TATGAGATTA CACGAGGGTG TTTTCTTCAA     300
AGGAAAGAGG GGAGAGTGAG GGGATAATGA TTTAAGGTTT CGGCCGTTCA TTATTTTTTC     360
TTCTCCCCCA GTTATCAAGT                                                 380
```

(2) INFORMATION FOR SEQ ID NO: 5:

(i) SEQUENCE CHARACTERISTICS:
        (A) LENGTH: 451 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
CAGAGTTCAT GCCCGAAAGG GTAGACCTCC CACCCTTGTG TATTATTACT TTGTTGCTTT      60
GGCGAGCTGC TTTCGGGCCT TGTATGCTCG CCAGAGAATA CCAAAACTCT TTTTATTAAT     120
GTCGTCTGAG TACTATATAA TAGTTAAAAC TTTCAACAAC GGATCTCTTG GTTCTGGCAT     180
CGATGAAGAA CGCAGCGAAA TGCGATAAGT AATGTGAATT GCAGAATTCA GTGAATCATC     240
GAATCTTTGA ACGCACATTG CGCCCCTTGG TATTCCGGGG GCATGCCTG TTCGAGCGTC      300
ATTTCAACCC TCAAGCTTAG CTTGGTATTG AGTCTATGTC AGTAATGGCA GGCTCTAAAA     360
```

```
TCAGTGGCGG CGCCGCTGGG TCCTGAACGT AGTAATATCT CTCGTTACAG GTTCTCGGTG       420

TGCTTCTGCC AAAACCCAAA TTTTTCTATG G                                     451

(2) INFORMATION FOR SEQ ID NO: 6:

(i) SEQUENCE CHARACTERISTICS:
         (A) LENGTH: 498 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 6:

CCGAGTGAGG GCCCTCTGGG TCCAACCTCC CACCCGTGTT TATTTTACCT TGTTGCTTCG        60

GCGGGCCCGC CTTAACTGGC CGCCGGGGGG CTTACGCCCC CGGGCCCGCG CCCGCCGAAG       120

ACACCCTCGA ACTCTGTCTG AAGATTGAAG TCTGAGTGAA AATATAAATT ATTTAAAACT       180

TTCAACAACG GATCTCTTGG TTCCGGCATC GATGAAGAAC GCAGCGAAAT GCGATACGTA       240

ATGTGAATTG CAAATTCAGT GAATCATCGA GTCTTTGAAC GCACATTGCG CCCCTGGTA       300

TTCCGGGGGG CATGCCTGTC CGAGCGTCAT TGCTGCCCTC AAGCCCGGCT TGTGTGTTGG       360

GCCCCGTCCC CCGATCTCCG GGGACGGGC CCGAAAGGCA GCGGCGGCAC CGCGTCCGGT       420

CCTCGAGCGT ATGGGGCTTT GTCACCCGCT CTGTAGGCCC GGCCGGCGCT TGCCGATCAA       480

CCCAAATTTT TATCCAGG                                                    498

(2) INFORMATION FOR SEQ ID NO: 7:

(i) SEQUENCE CHARACTERISTICS:
         (A) LENGTH: 556 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO: 7:

CCGAGTGAGG GCCCTTTGGG TCCAACCTCC CACCCGTGTT TATTTACCTC GTTGCTTCGG        60

CGGGCCCGCC TTAACTGGCC GCCGGGGGC TCACGCCCCC GGGCCCGCGC CGCCGAAGA        120

CACCCCCGAA CTCTGCCTGA AGATTGTCGT CTGAGTGAAA ATATAAATTA TTTAAAACTT       180

TCAACAACGG ATCTCTTGGT TCCGGCATCG ATGAAGAACG CAGCGAAATG CGATACGTAA       240

TGTGAATTGC AAATTCAGTG AATCATCGAG TCTTTGAACG CACATTGCGC CCCTGGTAT       300

TCCGGGGGGC ATGCCTGTCC GAGCGTCATT GCTGCCCTCA AGCCCGGCTT GTGTGTTGGG       360

CCCCGTCCTC CGATTCCGGG GACGGGCCC GAAAGGCAGC GGCGGCACCG CGTCCGGTCC       420

TCGAGCGTAT GGGGCTTTGT CACCCGCTCT GTAGGCCCGG CCGGCGCTTG CCGATCAACC       480

CAAATTTTTA TCCAGGTTGA CCTCGGATCA GGTAGGGATA CCCGCTGAAC TTAAGCATAT       540

CAATAAGCGG AGGAAA                                                      556

(2) INFORMATION FOR SEQ ID NO: 8:

(i) SEQUENCE CHARACTERISTICS:
         (A) LENGTH: 661 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO: 8:

```
GATTGAATTA TCATTGTTGC TCGAGTTCTA GTTTTAGATC TTTTACAATA ATGTGTATCT        60

TTATTGAAGA TGTGCGCTTA ATTGCGCTGC TTTTTTAAAG TGTCGCAGTA GAAGTAATCT       120

TGCTTGAATC TCAGTCAACG TTTACACACA TTGGAGTTTT TTTACTTTAA TTTAATTCTT       180

TCTGCTTTGA ATCGAAAGGT TCAAGGCAAA AAACAAACAC AAACAATTTT ATTTTATTAT       240

AATTTTTTAA ACTAAACCAA AATTCCTAAC GGAAATTTTA AAATAATTTA AAACTTTCAA       300

CAACGGATCT CTTGGTTCTC GCATCGATGA AGAACGTAGC GAATTGCGAT AAKTAATGTG       360

AATTGCAGAT ACTCGTGAAT CATTGAATTT TTGAACGCAC ATTGCGCCCT TGAGCATTCT       420

CAAGGGCATG CCTGTTTGAG CGTCATTTCC TTCTCAAAAG ATAATTTTTT ATTTTTTGGT       480

TGTGGGCGAT ACTCAGGGTT AGCTTGAAAT TGAAGATTGT TTCAATCTTT TTTAATTCAA       540

CACTTAGCTT CTTTGGAGAC GCTGTTCTCG CTGTGATGTA TTTATGAATT TATTCGTTTT       600

ACTTTACAAG GGAAATGGTA ATGTACCTTA GGCAAAGGGT TGCTTTTAAT ATTCATCAAG       660

T                                                                      661
```

(2) INFORMATION FOR SEQ ID NO: 9:

(i) SEQUENCE CHARACTERISTICS:
        (A) LENGTH: 547 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
CAGTATTCTT TTTGCCAGCG CTTAACTGCG CGGCGAAATA AACCTTACAC ACAATGTTTTT       60

TTGTTATTAC AGGAACTTTT GCTTTGGCTT GTCTCTAGAA ATAGAGTTGG GCCAAAGGTT      120

TAAACTAACT TCAATTTATT TGAACTATTT TTCTTATTGA AATGTCACTT TGTTGATTAA      180

ATTCAAAAAA TCTTCAAAAC TTTCAACAAC GGATCTCTTG GTTCTCGCAT CGATGAAGAA      240

CGCAGCGAAA TGCGATAAGT AATATGAATT GCAGATTTTC GTGAATCATC GAATCTTTGA      300

ACGCACATTG CGCCCTTTGG TATTCCAAAG GGCATGCCTG TTTGAGCGTC ATTTCTCTCT      360

CAAACCTTAG GGTTTGGTAT TGAGTGATAC TCTTAGTCGA ACTAGGCGTT TGCTTGAAAT      420

GTATCGGCAT GAGTGGTACT AGATTAGTGC TTCAGATTTT TCAATGTATT AGGTTTATCC      480

AACTCGTTGA ATAGTCTGAT GGCAAGTGTT TAGTAACTAT GGCTCGGCCT AACAACAACA      540

AACAAGT                                                                547
```

(2) INFORMATION FOR SEQ ID NO: 10:

(i) SEQUENCE CHARACTERISTICS:
        (A) LENGTH: 529 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
TAGTATTCTA TTGCCAGCGC TTAATTGCGC GGCGATAAAC CTTACACACA TTGTCTAGTT       60

TTTTTGAACT TTGCTTTGGG TGGTGAGCCT GGCTTACTGC CCAAAGGTCT AAACACATTT      120

TTTTAATGTT AAAACCTTTA ACCAATAGTC ATGAAAATTT TTAACAAAAA TTAAAATCTT      180
```

```
CAAAACTTTC AACAACGGAT CTCTTGGTTC TCGCAACGAT GAAGAACGCA GCGAAATGCG    240

ATACGTATTG TGAATTGCAG ATTTTCGTGA ATCATCGAAT CTTTGAACGC ACATTGCACC    300

CTCTGGTATT CCAGAGGGTA TGCCTGTTTG AGCGTCATTT CTCTCTCAAA CCTTCGGGTT    360

TGGTATTGAG TGATACTCTG TCAAGGGTTA ACTTGAAATA TTGACTTAGC AAGAGTGTAC    420

TAATAAGCAG TCTTTCTGAA ATAATGTATT AGGTTCTTCC AACTCGTTAT ATCAGCTAGG    480

CAGGTTTAGA AGTATTTTAG GCTCGGCTTA ACAACAATAA ACTAAAAGT               529
```

(2) INFORMATION FOR SEQ ID NO: 11:

(i) SEQUENCE CHARACTERISTICS:
        (A) LENGTH: 355 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
CTGTGATTTA TATCTTATAC ACATGCGTGA GCGCACCAAA CACCTAAAAT TGTAATAATAA    60

CCAGTCACTA AGTTTTAACA AAACAAAACT TTCAACAACG GATCTCTTGG TTCTCGCATC    120

GATGAAGAGC GCAGCGAAAT GCGATACCTA GTGTGAATTG CAGCCATCGT GAATCATCGA    180

GTTCTTGAAC GCACATTGCG CCCCATGGTA TTCCATGGGG CATGCCTGTC TGAGCGTCGT    240

TTCCTTCTTG CGCAAGCAGA GTTGAGAACA GGCTATGCCT TTTTCGAAAT GGAACGTCGT    300

GGACGAAGTG AACTAAACTT TTAGCACGCT TTGGCCGCCG AACTTTTAAC TAAGC        355
```

(2) INFORMATION FOR SEQ ID NO: 12:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
CTGTGATTTA CTACTACACT GCGTGAGCGG AACGAAAACA ACAACACCTA AAATGTGGAA    60

TATAGCATAT AGTCGACAAG AGAAATCTAC GAAAAAACAA ACAAAACTTT CAACAACGGA    120

TCTCTTGGTT CTCGCATCGA TGAAGAGCGC AGCGAAATGC GATACCTAGT GTGAATTGCA    180

GCCATCGTGA ATCATCGAGT TCTTGAACGC ACATTGCGCC CCTCGGCATT CCGGGGGGCA    240

TGCCTGTTTG AGCGTCGTTT CCATCTTGCG CGTGCGCAGA GTTGGGGGAG CGGAGCGGAC    300

GACGTGTAAA GAGCGTCGGA GCTGCGACTC GCCTGAAAGG GAGCGAAGCT GGCCGAGCGA    360

ACTAGACTTT TTTTCAGGGA CGCTTGGCGG CCGAGAGCGA GTGTTGCGAG ACAACAAAAA    420

GC                                                                  422
```

(2) INFORMATION FOR SEQ ID NO: 13:

(i) SEQUENCE CHARACTERISTICS:
        (A) LENGTH: 361 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
AAGAAATTTA ATAATTTTGA AAATGGATTT TTTTGTTTTG GCAAGAGCAT GAGAGCTTTT    60

ACTGGGCAAG AAGACAAGAG ATGGAGAGTC CACCCGGGCC TGCGCTTAAG TGCGCGGTCT   120

TGCTAGGCTT GTAAGTTTCT TTCTTGCTAT TCCAAACGGT GAGAGATTTC TGTGCTTTTG   180

TTATAGGACA ATTAAAACCG TTTCAATACA ACACACTGTG GAGTTTTCAT ATCTTTGCAA   240

CTTTTTCTTT GGGCATTCGA GCAATCGGGG CCCAGAGGTA ACAAACACAA ACAATTTTAT   300

CTATTCATTA AATTTTTGTC AAAAACAAGA ATTTTCGTAA CTGGAAATTT TAAAATATTA   360

A                                                                  361

(2) INFORMATION FOR SEQ ID NO: 14:

(i) SEQUENCE CHARACTERISTICS:
        (A) LENGTH: 235 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

CCTTCTCAAA CATTCTGTTT GGTAGTGAGT GATACTCTTT GGAGTTAACT TGAAATTGCT    60

GGCCTTTTCA TTGGATGTTT TTTTTTCCAA AGAGAGGTT CTCTGCGTGC TTGAGGTATA   120

ATGCAAGTAC GGTCGTTTTA GGTTTTACCA ACTGCGGCTA ATCTTTTTTT ATACTGAGCG   180

TATTGGAACG TTATCGATAA GAAGAGAGCG TCTAGGCGAA CAATGTTCTT AAAGT       235

(2) INFORMATION FOR SEQ ID NO: 15:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

AAGAAAAAAA CTGTTTATAA ACAGACGGTA GACTTTTCTT GGGGAGAGGT TGTTGATTGC    60

TTTGGCCTGC GCTTAACTGC GCGGCTAGTA GTTGATGATT TTGTTATTAT CCAGACGAA   120

GGAAACGTCT GATTTTAAAA ACATTATACA CTTTGGAGTA CTTTTTTTAA TGTATTTCTT   180

CCTTGGACGA GCAATTGTTC AAGGGTCAAT AAACACAAAC AATTTTTTTT TTATTTAAAT   240

TTAAAATAAT TCAAAATATA TCATTTCTTT TATTAGGAAT ATAAAAATTT TA          292

(2) INFORMATION FOR SEQ ID NO: 16:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

CCTTCTCAAA AGAGTTTTTT TATTCTTTTG GTTGTGAGTG ATACTCTTTC CTTTTACAGG    60

GAAGGGGTTA ACTTGAAATT GTTGCCTAGC AAAGAAGAAT TTTGATTGAA ATTTCTTGTT   120

TATTACTATT AGGTTTATCC CAACTAGTGA TTATTGAGAG TTTTTATTAC AGAGTCTTTT   180

CACTTGCTAT AATACTATTC TATAAGT                                      207
```

(2) INFORMATION FOR SEQ ID NO: 17:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

```
CAGGATGCTG GGCGCAAGCC CGTGCAGACA CGTGGATAAG CAAGGATAAA AATACATTAA      60

ATTTATTTAG TTTAGTCAAG AAAGAATTTT A                                    91
```

(2) INFORMATION FOR SEQ ID NO: 18:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

```
CCTTCTCACT ATTTAGTGGT TATGAGATTA CACGAGGGTG TTTTCTTCAA AGGAAAGAGG      60

GGAGAGTGAG GGGATAATGA TTTAAGGTTT CGGCCGTTCA TTATTTTTTT CTTCTCCCCC     120

AGTTATCAAG T                                                         131
```

(2) INFORMATION FOR SEQ ID NO: 19:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

```
CAGGATGCTG GGCGCAAGCC CGTGCAGACA CGTGGATAAG TAAGGATAAA AATACATTAA      60

ATTTATTTAG TTTTAGTCAA GAAAGAATTT TA                                   92
```

(2) INFORMATION FOR SEQ ID NO: 20:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
CCTTCTCACT ATTTAGTGGT TATGAGATTA CACGAGGGTG TTTTCTTCAA AGGAAAGAGG      60

GGAGAGTGAG GGGATAATGA TTTAAGGTTT CGGCCGTTCA TTATTTTTC TTCTCCCCCA      120

GTTATCAAGT                                                           130
```

(2) INFORMATION FOR SEQ ID NO: 21:

(i) SEQUENCE CHARACTERISTICS:
        (A) LENGTH: 146 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 21:

```
CAGAGTTCAT GCCCGAAAGG GTAGACCTCC CACCCTTGTG TATTATTACT TTGTTGCTTT      60

GGCGAGCTGC TTTCGGGCCT TGTATGCTCG CCAGAGAATA CCAAAACTCT TTTTATTAAT     120

GTCGTCTGAG TACTATATAA TAGTTA                                          146
```

(2) INFORMATION FOR SEQ ID NO: 22:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
CAACCCTCAA GCTTAGCTTG GTATTGAGTC TATGTCAGTA ATGGCAGGCT CTAAAATCAG      60

TGGCGGCGCC GCTGGGTCCT GAACGTAGTA ATATCTCTCG TTACAGGTTC TCGGTGTGCT     120

TCTGCCAAAA CCCAAATTTT TCTATGG                                         147
```

(2) INFORMATION FOR SEQ ID NO: 23:

(i) SEQUENCE CHARACTERISTICS:
        (A) LENGTH: 175 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

```
CCGAGTGAGG GCCCTCTGGG TCCAACCTCC CACCCGTGTT TATTTTACCT TGTTGCTTCG      60

GCGGGCCCGC CTTAACTGGC CGCCGGGGGG CTTACGCCCC CGGGCCCGCG CCCGCCGAAG     120

ACACCCTCGA ACTCTGTCTG AAGATTGAAG TCTGAGTGAA AATATAAATT ATTTA          175
```

(2) INFORMATION FOR SEQ ID NO: 24:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
CTGCCCTCAA GCCCGGCTTG TGTGTTGGGC CCCGTCCCCC GATCTCCGGG GGACGGGCCC      60

GAAAGGCAGC GGCGGCACCG CGTCCGGTCC TCGAGCGTAT GGGGCTTTGT CACCCGCTCT     120

GTAGGCCCGG CCGGCGCTTG CCGATCAACC CAAATTTTTA TCCAGG                    166
```

(2) INFORMATION FOR SEQ ID NO: 25:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

| | | | |
|---|---|---|---|
| CCGAGTGAGG GCCCTTTGGG TCCAACCTCC CACCCGTGTT TATTTACCTC GTTGCTTCGG | 60 |
| CGGGCCCGCC TTAACTGGCC GCCGGGGGGC TCACGCCCCC GGGCCCGCGC CCGCCGAAGA | 120 |
| CACCCCCGAA CTCTGCCTGA AGATTGTCGT CTGAGTGAAA ATATAAATTA TTTA | 174 |

(2) INFORMATION FOR SEQ ID NO: 26:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

| | |
|---|---|
| CTGCCCTCAA GCCCGGCTTG TGTGTTGGGC CCCGTCCTCC GATTCCGGGG GACGGGCCCG | 60 |
| AAAGGCAGCG GCGGCACCGC GTCCGGTCCT CGAGCGTATG GGGCTTTGTC ACCCGCTCTG | 120 |
| TAGGCCCGGC CGGCGCTTGC CGATCAACCC AAATTTTTAT CCAGG | 165 |

(2) INFORMATION FOR SEQ ID NO: 27:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

| | |
|---|---|
| GATTGAATTA TCATTGTTGC TCGAGTTCTA GTTTTAGATC TTTTACAATA ATGTGTATCT | 60 |
| TTATTGAAGA TGTGCGCTTA ATTGCGCTGC TTTTTTAAAG TGTCGCAGTA GAAGTAATCT | 120 |
| TGCTTGAATC TCAGTCAACG TTTACACACA TTGGAGTTTT TTTACTTTAA TTTAATTCTT | 180 |
| TCTGCTTTGA ATCGAAAGGT TCAAGGCAAA AAACAAACAC AAACAATTTT ATTTTATTAT | 240 |
| AATTTTTTAA ACTAAACCAA AATTCCTAAC GGAAATTTTA AAATAATTTA | 290 |

(2) INFORMATION FOR SEQ ID NO: 28:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 28:

| | |
|---|---|
| CCTTCTCAAA AGATAATTTT TTATTTTTTG GTTGTGGGCG ATACTCAGGG TTAGCTTGAA | 60 |
| ATTGAAGATT GTTTCAATCT TTTTTAATTC AACACTTAGC TTCTTTGGAG ACGCTGTTCT | 120 |
| CGCTGTGATG TATTTATGAA TTTATTCGTT TTACTTTACA AGGGAAATGG TAATGTACCT | 180 |
| TAGGCAAAGG GTTGCTTTTA ATATTCATCA AGT | 213 |

(2) INFORMATION FOR SEQ ID NO: 29:

(i) SEQUENCE CHARACTERISTICS:
        (A) LENGTH: 196 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO: 29:

```
CAGTATTCTT TTTGCCAGCG CTTAACTGCG CGGCGAAATA AACCTTACAC ACAATGTTTT      60

TTGTTATTAC AGGAACTTTT GCTTTGGCTT GTCTCTAGAA ATAGAGTTGG GCCAAAGGTT     120

TAAACTAACT TCAATTTATT TGAACTATTT TTCTTATTGA AATGTCACTT TGTTGATTAA     180

ATTCAAAAAA TCTTCA                                                     196
```

(2) INFORMATION FOR SEQ ID NO: 30:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 30:

```
CTCTCTCAAA CCTTAGGGTT TGGTATTGAG TGATACTCTT AGTCGAACTA GGCGTTTGCT      60

TGAAATGTAT CGGCATGAGT GGTACTAGAT TAGTGCTTCA GATTTTTCAA TGTATTAGGT     120

TTATCCAACT CGTTGAATAG TCTGATGGCA AGTGTTTAGT AACTATGGCT CGGCCTAACA     180

ACAACAAACA AGT                                                        193
```

(2) INFORMATION FOR SEQ ID NO: 31:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 31:

```
TAGTATTCTA TTGCCAGCGC TTAATTGCGC GGCGATAAAC CTTACACACA TTGTCTAGTT      60

TTTTTGAACT TTGCTTTGGG TGGTGAGCCT GGCTTACTGC CCAAAGGTCT AAACACATTT     120

TTTTAATGTT AAAACCTTTA ACCAATAGTC ATGAAAATTT TTAACAAAAA TTAAAATCTT     180

CA                                                                    182
```

(2) INFORMATION FOR SEQ ID NO: 32:

(i) SEQUENCE CHARACTERISTICS:
        (A) LENGTH: 189 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

```
CTCTCTCAAA CCTTCGGGTT TGGTATTGAG TGATACTCTG TCAAGGGTTA ACTTGAAATA      60

TTGACTTAGC AAGAGTGTAC TAATAAGCAG TCTTTCTGAA ATAATGTATT AGGTTCTTCC     120

AACTCGTTAT ATCAGCTAGG CAGGTTTAGA AGTATTTTAG GCTCGGCTTA ACAACAATAA     180

ACTAAAAGT                                                             189
```

(2) INFORMATION FOR SEQ ID NO: 33:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

CTGTGATTTA TATCTTATAC ACATGCGTGA GCGCACCAAA CACCTAAAAT TGTAATAATA      60

CCAGTCACTA AGTTTTAACA AAACA      85

(2) INFORMATION FOR SEQ ID NO: 34:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 34:

CCTTCTTGCG CAAGCAGAGT TGAGAACAGG CTATGCCTTT TTCGAAATGG AACGTCGTGG      60

ACGAAGTGAA CTAAACTTTT AGCACGCTTT GGCCGCCGAA CTTTTAACTA AGC      113

(2) INFORMATION FOR SEQ ID NO: 35:

(i) SEQUENCE CHARACTERISTICS:
        (A) LENGTH: 103 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 35:

CTGTGATTTA CTACTACACT GCGTGAGCGG AACGAAAACA ACAACACCTA AAATGTGGAA      60

TATAGCATAT AGTCGACAAG AGAAATCTAC GAAAAAACAA ACA      103

(2) INFORMATION FOR SEQ ID NO: 36:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 36:

CCATCTTGCG CGTGCGCAGA GTTGGGGGAG CGGAGCGGAC GACGTGTAAA GAGCGTCGGA      60

GCTGCGACTC GCCTGAAAGG GAGCGAAGCT GGCCGAGCGA ACTAGACTTT TTTTCAGGGA     120

CGCTTGGCGG CCGAGAGCGA GTGTTGCGAG ACAACAAAAA GC      162

(2) INFORMATION FOR SEQ ID NO: 37:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 37:

TTTTGGCAAG AGCATGAGAG CTTTTACTGG GCAAGAAGAC AAGAGATGGA GAGTCCACCC    60

(2) INFORMATION FOR SEQ ID NO: 38:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 38:

CCGTACTTGC ATTATACCTC AAGCACGCAG AGAAACCTCT CTTTGGAAAA AAAAACA    57

(2) INFORMATION FOR SEQ ID NO: 39:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 39:

TGGCAAGAGC ATGAGAGCTT TTACTGGGCA AGAAGACAAG AGATGGAGAG TCCACCCGGG    60

(2) INFORMATION FOR SEQ ID NO: 40:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 40:

CGACCGTACT TGCATTATAC CTCAAGCACG CAGAGAAACC TCTCTTTGGA AAAAAAAAC    59

(2) INFORMATION FOR SEQ ID NO: 41:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 41:

CTGTTTATAA ACAGACGGTA GACTTTTCTT GGGGAGAGGT TGTTGATTGC TTTGGCCTGC    60

GCTTAACTGC GCGGCTAGTA GTTGATGATT TTGTTATTAT CCGAGACGAA    110

(2) INFORMATION FOR SEQ ID NO: 42:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 42:

TAATAAAAAC TCTCAATAAT CACTAGTTGG GATAAACCTA ATAGTAATAA ACAAGAAATT    60

(2) INFORMATION FOR SEQ ID NO: 43:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 43:

TTTATAAACA GACGGTAGAC TTTTCTTGGG GAGAGGTTGT TGATTGCTTT GGCCTG    56

(2) INFORMATION FOR SEQ ID NO: 44:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 44:

CTGTAATAAA AACTCTCAAT AATCACTAGT TGGGATAAAC CTAATAGTAA TAAACAAGAA    60
AT    62

(2) INFORMATION FOR SEQ ID NO: 45:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 45:

GGTGAACCTG CGGAAGGATC ATTACAGGAT GCTGGGCGCA AGCCCGTGCA GACACGTGGA    60
TAAGCAAGGA TAAAAATACA T    81

(2) INFORMATION FOR SEQ ID NO: 46:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 46:

ACTGGGGGAG AAGAAAAAAA TAATGAACGG CCGAAACCTT AAATCATTAT CCCCTCACTC    60
TCCCCTCTTT CCTTTGAAGA AAACACCCTC GTGTAATCTC ATAACCACTA    110

(2) INFORMATION FOR SEQ ID NO: 47:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

GGTGAACCTG CGGAAGGATC ATTACAGGAT GCTGGGCGCA AGCCCGTGCA GACACG         56

(2) INFORMATION FOR SEQ ID NO: 48:

(i) SEQUENCE CHARACTERISTICS:
       (A) LENGTH: 110 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 48:

AACTGGGGGA GAAGAAAAAA TAATGAACGG CCGAAACCTT AAATCATTAT CCCCTCACTC       60

TCCCCTCTTT CCTTTGAAGA AAACACCCTC GTGTAATCTC ATAACCACTA                110

(2) INFORMATION FOR SEQ ID NO: 49:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 49:

TGGCGAGCTG CTTTCGGGCC TTGTATGCTC GCCAGAGAAT ACCAAAACTC TTTTTAT          57

(2) INFORMATION FOR SEQ ID NO: 50:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 50:

GCGCCGCCAC TGATTTTAGA GCCTGCCATT ACTGACATAG ACTCAATACC AAGCTAA          57

(2) INFORMATION FOR SEQ ID NO: 51:

(i) SEQUENCE CHARACTERISTICS:
       (A) LENGTH: 57 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 51:

GCTGCTTTCG GGCCTTGTAT GCTCGCCAGA GAATACCAAA ACTCTTTTTA TTAATGT          57

(2) INFORMATION FOR SEQ ID NO: 52:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 52:

```
CCCTYTGGGT CCAACCTCCC ACCCGTGTTT ATTTTACCTT GTTGCTTCGG CGGGCCCGCC        60
```

(2) INFORMATION FOR SEQ ID NO: 53:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 53:

```
TCGGCAAGCG CCGGCCGGGC CTACAGAGCG GGTGACAAAG CCCCATACGC TCGAGGACCG        60

GACGCGGTGC                                                               70
```

(2) INFORMATION FOR SEQ ID NO: 54:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 54:

```
CCCTYTGGGT CCAACCTCCC ACCCGTGTTT ATTTTACCTT GTTGCTTCGG CGGGCCCGC         59
```

(2) INFORMATION FOR SEQ ID NO: 55:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 55:

```
AGCGCCGGCC GGGCCTACAG AGCGGGTGAC AAAGCCCCAT ACGCTCGAGG ACCGG            55
```

(2) INFORMATION FOR SEQ ID NO: 56:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 56:

```
AATCTTGCTT GAATCTCAGT CAACGTTTAC ACACATTGGA GTTTTTTTAC TTTAATTTAA        60

TTCTTTCTGC TTTGAATCGA AAGGTTCAAG GCAAAAAAC                               99
```

(2) INFORMATION FOR SEQ ID NO: 57:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 57:

```
TAAATACATC ACAGCGAGAA CAGCGTCTCC AAAGAAGCTA AGTGTTGAAT TAAAAAAGAT    60

T                                                                  61
```

(2) INFORMATION FOR SEQ ID NO: 58:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 58:

```
CTCATGCCGA TACATTTCAA GCAAACGCCT AGTTCGACTA AGAGTATCAC TCAATACCAA    60

A                                                                  61
```

(2) INFORMATION FOR SEQ ID NO: 59:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 59:

```
TAAACACTTG CCATCAGACT ATTCAACGAG TTGGATAAAC CTAATACATT GAAAAATCTG    60

A                                                                  61
```

(2) INFORMATION FOR SEQ ID NO: 60:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 60:

```
TTGCTTTGGG TGGTGAGCCT GGCTTACTGC CCAAAGGTCT AAACACATTT TTTTAATGT     59
```

(2) INFORMATION FOR SEQ ID NO: 61:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 61:

```
ATACATTATT TCAGAAAGAC TGCTTATTAG TACACTCTTG CTAAGTCAAT ATTTCAAGTT    60

A                                                                  61
```

(2) INFORMATION FOR SEQ ID NO: 62:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 62:

GCGGCCAAAG CGTGCTAAAA GTTTAGTTCA CTTCGTCCAC GACGTTCCAT TTCGAAAAAG    60

G    61

(2) INFORMATION FOR SEQ ID NO: 63:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 63:

GCGGAACGAA AACAACAACA CCTAAAATGT GGAATATAGC ATATAGTCGA CAAGAGAAAT    60

C    61

(2) INFORMATION FOR SEQ ID NO: 64:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 64:

TCAGGCGAGT CGCAGCTCCG ACGCTCTTTA CACGTCGTCC GCTCCGCTCC CCCAACTCT    59

(2) INFORMATION FOR SEQ ID NO: 65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 65:

CTTTTACTGG GCAAGAAGAC    20

(2) INFORMATION FOR SEQ ID NO: 66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 66:

AAGCACGCAG AGAAACC    17

(2) INFORMATION FOR SEQ ID NO: 67:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 67:

TTACTGGGCA AGAAGACAAG                    20

(2) INFORMATION FOR SEQ ID NO: 68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 68:

CTCAAGCACG CAGAGAA                       17

(2) INFORMATION FOR SEQ ID NO: 69:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 69:

GACTTTTCTT GGGGAGAG                      18

(2) INFORMATION FOR SEQ ID NO: 70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 70:

TCACTAGTTG GGATAAACCT                    20

(2) INFORMATION FOR SEQ ID NO: 71:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 71:

TTTTCTTGGG GAGAGG                        16

(2) INFORMATION FOR SEQ ID NO: 72:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 72:

```
ATCACTAGTT GGGATAAACC                                                     20

(2) INFORMATION FOR SEQ ID NO: 73:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 73:

CGGCTAGTAG TTGATGATT                                                      19

(2) INFORMATION FOR SEQ ID NO: 74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 74:

CACTAGTTGG GATAAACCTA                                                     20

(2) INFORMATION FOR SEQ ID NO: 75:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 75:

ATTACAGGAT GCTGGGC                                                        17

(2) INFORMATION FOR SEQ ID NO: 76:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 76:

ATTACAGGAT GCTGGG                                                         16

(2) INFORMATION FOR SEQ ID NO: 77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 77:

CGTGCAGACA CGTGGAT                                                        17

(2) INFORMATION FOR SEQ ID NO: 78:
```

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 78:

CTTTGAAGAA AACACCCTC                                                    19

(2) INFORMATION FOR SEQ ID NO: 79:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 79:

AATCATTATC CCCTCACTC                                                    19

(2) INFORMATION FOR SEQ ID NO: 80:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 80:

TAATGAACGG CCGAAAC                                                      17

(2) INFORMATION FOR SEQ ID NO: 81:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 81:

TTGTATGCTC GCCAGAG                                                      17

(2) INFORMATION FOR SEQ ID NO: 82:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 82:

GCCTGCCATT ACTGACA                                                      17

(2) INFORMATION FOR SEQ ID NO: 83:

(i) SEQUENCE CHARACTERISTICS:
            (A) LENGTH: 17 base pairs
            (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO: 83:

GCTCGCCAGA GAATACC                                                  17

(2) INFORMATION FOR SEQ ID NO: 84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 84:

ACCCGTGTTT ATTTTACCTT                                               20

(2) INFORMATION FOR SEQ ID NO: 85:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 85:

CTACAGAGCG GGTGACA                                                  17

(2) INFORMATION FOR SEQ ID NO: 86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 86:

CACCCGTGTT TATTTTACCT                                               20

(2) INFORMATION FOR SEQ ID NO: 87:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 87:

CAAAGCCCCA TACGC                                                    15

(2) INFORMATION FOR SEQ ID NO: 88:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 88:

AGCGGGTGAC AAAGC                                            15

(2) INFORMATION FOR SEQ ID NO: 89:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 89:

CAACGTTTAC ACACATTGG                                        19

(2) INFORMATION FOR SEQ ID NO: 90:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 90:

AATTCTTTCT GCTTTGAATC G                                     21

(2) INFORMATION FOR SEQ ID NO: 91:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 91:

CAGCGTCTCC AAAGAAGCTA A                                     21

(2) INFORMATION FOR SEQ ID NO: 92:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 92:

GCAAACGCCT AGTTCGACTA A                                     21

(2) INFORMATION FOR SEQ ID NO: 93:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

ATTCAACGAG TTGGATAAAC C                                     21

(2) INFORMATION FOR SEQ ID NO: 94:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 94:

GGCTTACTGC CCAAAGGTC                                     19

(2) INFORMATION FOR SEQ ID NO: 95:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 95:

TGCTTATTAG TACACTCTTG C                                 21

(2) INFORMATION FOR SEQ ID NO: 96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 96:

GTTTAGTTCA CTTCGTCCAC G                                 21

(2) INFORMATION FOR SEQ ID NO: 97:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:

CCTAAAATGT GGAATATAGC A                                 21

(2) INFORMATION FOR SEQ ID NO: 98:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

ACGCTCTTTA CACGTCGTC                                     19

(2) INFORMATION FOR SEQ ID NO: 99:

-continued

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

GGAAGTAAAA GTCGTAACAA GG                                              22

(2) INFORMATION FOR SEQ ID NO: 100:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

TCCTCCGCTT ATTGATATGC                                                 20
```